United States Patent
Hansson et al.

(10) Patent No.: US 7,258,672 B2
(45) Date of Patent: Aug. 21, 2007

(54) SYSTEM AND METHOD FOR AUTOMATIC TAKING OF SPECIMENS

(75) Inventors: Hans-Axel Hansson, Lund (SE); Jens Hansson, Lund (SE)

(73) Assignee: DiLab i Lund AB, Lund (SE)

( * ) Notice: Subject to any disclaimer, the term of this patent is extended or adjusted under 35 U.S.C. 154(b) by 465 days.

(21) Appl. No.: 10/432,574

(22) PCT Filed: Nov. 30, 2001

(86) PCT No.: PCT/SE01/02639

§ 371 (c)(1),
(2), (4) Date: Oct. 17, 2003

(87) PCT Pub. No.: WO02/43589

PCT Pub. Date: Jun. 6, 2002

(65) Prior Publication Data

US 2004/0068202 A1    Apr. 8, 2004

(30) Foreign Application Priority Data

Nov. 30, 2000 (SE) .................... 0004431
Aug. 24, 2001 (SE) .................... 0102818

(51) Int. Cl.
*A61D 5/00*    (2006.01)

(52) U.S. Cl. .................... 600/581

(58) Field of Classification Search ............... 600/573, 600/576, 578, 580, 581; 604/164.02, 191
See application file for complete search history.

(56) References Cited

U.S. PATENT DOCUMENTS

| | | | | |
|---|---|---|---|---|
| 3,043,303 A | * | 7/1962 | Still ............................ | 604/66 |
| 3,457,957 A | * | 7/1969 | Mueller ................. | 137/625.68 |
| 3,650,093 A | * | 3/1972 | Rosenberg ...................... | 96/6 |
| 4,077,395 A | | 3/1978 | Woolner | |
| 4,517,302 A | | 5/1985 | Saros | |
| 4,657,027 A | | 4/1987 | Paulsen | |
| 4,691,580 A | | 9/1987 | Fosslien | |
| 4,696,309 A | * | 9/1987 | Stephan ...................... | 600/575 |
| 4,796,644 A | * | 1/1989 | Polaschegg ................. | 600/573 |
| 4,960,412 A | * | 10/1990 | Fink ...................... | 604/167.04 |
| 5,148,811 A | * | 9/1992 | Messinger ................. | 600/486 |
| 5,156,596 A | * | 10/1992 | Balbierz et al. ........ | 604/164.11 |

(Continued)

FOREIGN PATENT DOCUMENTS

DE    1 9617949    10/1997

(Continued)

*Primary Examiner*—Max Hindenburg
*Assistant Examiner*—Rene Towa
(74) *Attorney, Agent, or Firm*—Ladas & Parry LLP

(57) ABSTRACT

A method and a system for automatic taking of specimen from a static or living test object, comprising the steps and functional elements of guiding a specimen collector (10) by means of a guiding device (20) to a specimen terminal (22) attached to the test object (1); extracting a fluid specimen from the test object (1) to the specimen collector (10); guiding the specimen collector (10) by means of the guiding device (20) to a specimen container (50); and delivering or outputting the specimen from the specimen collector (10) to the specimen container (50).

17 Claims, 20 Drawing Sheets

U.S. PATENT DOCUMENTS

| | | | |
|---|---|---|---|
| 5,325,867 A * | 7/1994 | Skrabal et al. | 600/578 |
| 5,573,008 A * | 11/1996 | Robinson et al. | 600/567 |
| 5,649,547 A * | 7/1997 | Ritchart et al. | 600/566 |
| 5,816,256 A | 10/1998 | Kissinger et al. | |
| 5,827,305 A * | 10/1998 | Gordon | 606/159 |
| 5,865,766 A * | 2/1999 | Bonsall et al. | 600/578 |
| 5,879,334 A * | 3/1999 | Brimhall | 604/165.04 |
| 5,902,253 A * | 5/1999 | Pfeiffer et al. | 600/584 |
| 6,062,224 A | 5/2000 | Kissinger et al. | |
| 6,068,603 A * | 5/2000 | Suzuki | 600/565 |
| 6,071,408 A * | 6/2000 | Allington et al. | 210/634 |
| 6,113,554 A * | 9/2000 | Gilcher et al. | 600/573 |
| 6,736,783 B2 * | 5/2004 | Blake et al. | 600/582 |

FOREIGN PATENT DOCUMENTS

| | | |
|---|---|---|
| EP | 0389719 | 2/1997 |
| JP | 08-154923 | 6/1996 |
| WO | WO9625186 | 8/1996 |
| WO | WO9956630 | 11/1999 |

* cited by examiner

SYSTEM AND METHOD FOR AUTOMATIC TAKING OF SPECIMENS

TECHNICAL FIELD

The present invention relates generally to a system and a method for automatic taking of specimens from a test object in the shape of a living being. More specifically, the invention relates to such a system and method that handles the taking of a specimen in a manner that minimises unintentional contamination or separation of the specimen.

BACKGROUND

In medical science and pharmaceutical industry there is often a need for testing the reaction of drugs or treatments in living beings, for example test objects in the shape of laboratory animals such as rats and pigs used for experimental purposes. In such cases it is common to take a plurality of samples or specimens from the test object as well as injecting substances into the test object during the course of hours or days, in order to allow observation of gradual responses in the test object. In order to minimise time and cost consuming manual handling of taking specimen as well as the stress impact of such a manual handling on the laboratory animal, attempts have been made to automate the sample taking procedure. There is also an application in monitoring animals or humans being during medical treatment.

PRIOR ART

In prior art there are automatic systems for taking of specimens from and for delivering injections to living beings, for example laboratory animals used for experimental purposes such as rats and pigs. Such an automatic system is for example provided by the inventors of the present invention and is sold under the trademark AccuSampler. Such a prior art system includes a computer with accompanying computer program software for controlling the taking of specimens, injecting and communicating with a user as well as computer program software for storing and generating system parameters and log files. The system further includes actuating devices such as pumps, valves, containers for injection solutions, rinsing liquid and specimens, one or more catheters and a tubing system.

In this system the laboratory animal is before for example an automatic taking of blood samples provided with a catheter surgically inserted into the vessel from which specimen or samples are to be taken. This catheter is preferably coupled to a pivotal arm or a swivel that is suspended in a balance beam. The swivel is devised to enable freedom of movement for the laboratory animal. When taking a specimen, the catheter is connected to the tubing system via the swivel. The computer program software of the system controls all the activities involved in taking the specimen, delivering an injection and handling liquids. Through user interfaces it is possible for a user to define a scheme for taking of specimen and delivering injections, for example when and how often a specimen shall be taken or a substance shall be injected. It is also provided for storing information on the specimens that have been taken and the injections that have been made, for example when a specific specimen was taken or a specific substance was injected.

The prior art document EP 0 389 719 to International Technidyne Corp shows an example of a sample collection and delivery system of the described kind, wherein the samples are transported in a lumen of a tubing from one end to other with a separation between each sample. The sample thus passes through a long part of a tube.

Another piece of prior art, U.S. Pat. No. 4,077,395 to Woolner shows a sampling apparatus for automatically collecting samples from a patient. Samples are taken from the vascular system of a patient and are transported via a tubing to a plurality of collector vessels. Between the samples, the transport tube is flushed with saline solution.

The prior art document WO 96/25186 to Gensia Inc describes a feedback controlled drug delivery system including an automated blood sampling system. Also in this piece of prior art blood samples are transported in relatively long tubings.

In this kind of prior art systems the taken specimen or collected sample is transported through a sampling device and the tubing system, which entails a risk for adhesion of the taken specimen to the inside of the tubing system. This entails on one hand a risk for contamination along the inside of the tubing system and on the other hand a risk that the specimen that is transported through the tubing system attains another composition than that of the freshly specimen. The latter phenomenon can occur as a result of a selective separation dependent on the adhesive characteristics of the specimen. The result of this is thus that the specimen that is analysed may have other characteristics or properties than when it was taken. This can cause errors in for example pharmacokinetic studies, which concerns the time dependent change of the concentration of a specific pharmaceutical preparation in for example blood.

OBJECT OF THE INVENTION

The overall object of the present invention is to solve the problem of contamination and separation in a specimen taken and handled in an automatic system for taking specimen on a living test object.

More specifically the present invention seeks to minimise unintentional contamination and selective separation of a taken specimen due to adhesion of components of the specimen in the tubing system of such an automatic system.

SUMMARY OF THE INVENTION

The stated problem is solved by the present invention by guiding a specimen collector through a guiding device to a specimen terminal arranged on or attached to the living test object, for example a rat or a mouse or some other living being. The specimen terminal can for,example comprise a catheter inserted into a vessel of the test object. The specimen collector is docked or connected to the specimen terminal and a specimen is loaded from the test object into a specimen cavity located at the distal end of the specimen collector. Thereafter the specimen collector is guided back through the guiding device to a specimen container in which the specimen is delivered or unloaded. Testing or processing of the specimen can be conducted in or from the specimen container. The taken specimen is thus transported to the specimen container from the test object to the specimen container without having contact with any other material than that constituting the walls of the specimen cavity of the specimen collector. Thereby, the unintentional contamination and selective separation of specimens due to material contact is minimised.

The guiding device is coupled on one hand to the specimen terminal and on the other hand to the specimen container, respectively, by means of a mechanical connection. In accordance with an aspect of the invention, a fluid specimen is extracted from the living being to the specimen collector, for example by means of suction power actuated by a pumping device such as a piston pump or a roller pump.

The guiding device is in accordance with a further aspect provided with points or a path switch at a junction between a first guiding branch leading to the test object and a second guiding branch leading to the specimen container. Typically, after collecting or delivering a specimen the specimen collector is retracted behind the points, which switches the guide path to a selected branch and thereafter guides the specimen collector forwards down the path of the selected branch.

The invention preferably further comprises an attaching and positioning mechanism arranged at the specimen terminal and devised for attaching and position the specimen terminal and the guiding device to the test object.

In a preferred embodiment, the specimen collector is implemented by means of an inner tubing, which is guided co-axially inside an outer tubing comprised in the guiding device. The outer tubing is in one embodiment integrated with, i.e. made in one piece with or fastened to the attaching mechanism. In an embodiment being implemented by inner and outer tubing, the mentioned guiding branches are implemented by means of branch tubes and the points or switch is then preferably implemented by means of a tube guide that is displaceable in a radial direction.

A further aspect of the invention is directed to a computer program product for use in a data processing system and devised for controlling automatic specimen taking in accordance with the inventive method. The computer program product comprises computer program code portions, possibly stored on a storage medium and devised to control the data processing system to control the specimen taking apparatus to perform the steps of the inventive method.

Definitions

The distal and the proximal part of a component refer to the parts of the component that are farthest from and closest to the pumping device, respectively.

BRIEF DESCRIPTION OF THE DRAWINGS

The present invention is described in further detail below with reference to the accompanying drawings, wherein.

DETAILED DESCRIPTION OF EMBODIMENTS

System Overview

In its most general embodiment, the system in accordance with the invention comprises a specimen collector that is configured to be lead or guided by means of a guiding device coupled to a test object. The test object is in most cases a living being but possibly also some other test object that is the subject of repetitive taking of specimen. The described embodiments of the invention are directed to collecting, sampling or taking liquid specimen for example from a vessel in a living being or from some other kind of vessel containing a liquid. With a modification the specimen collector may be adapted to collect solid material samples or specimen from a test object.

After the taking of a specimen or sample, the specimen is temporarily stored in a cavity or specimen grip or storage at the distal end of the specimen collector. The specimen collector is thereafter by means of the guiding device lead to a specimen container such as a test glass or test tube where the specimen is delivered for storage or further processing. Embodiments of the inventive system can comprise one or a plurality of specimen containers testing tubes for fluid specimen, dependent on the specific application of the invention.

The specimen taking system and its functions in accordance with the inventive method is automatically controlled by means of computer program software being executed on a control data processing system. Specific test schemes are also controlled by such a computer program product, for example specimen taking dependent on a time schedule for collecting samples or specimen from the test object. The control data processing system may be a dedicated control data processor or a personal computer set up with a suitable control program. The user can through a user interface define the specimen taking procedure and different specimen taking parameters, for example by defining a selectable number of specimens to be taken with a selectable time interval or at specific points in time. There is also functional means configured for storing information on taken specimens, such as time and specimen identity. The computer program product comprises program code portions adapted to direct a data processing system to perform the steps of the inventive method or control the movements of the system components as described in this description. The computer program product preferably comprises a carrier in the shape of a storage medium, such as a diskette or CD or the like, for storing the inventive computer program portions.

Figure 1:
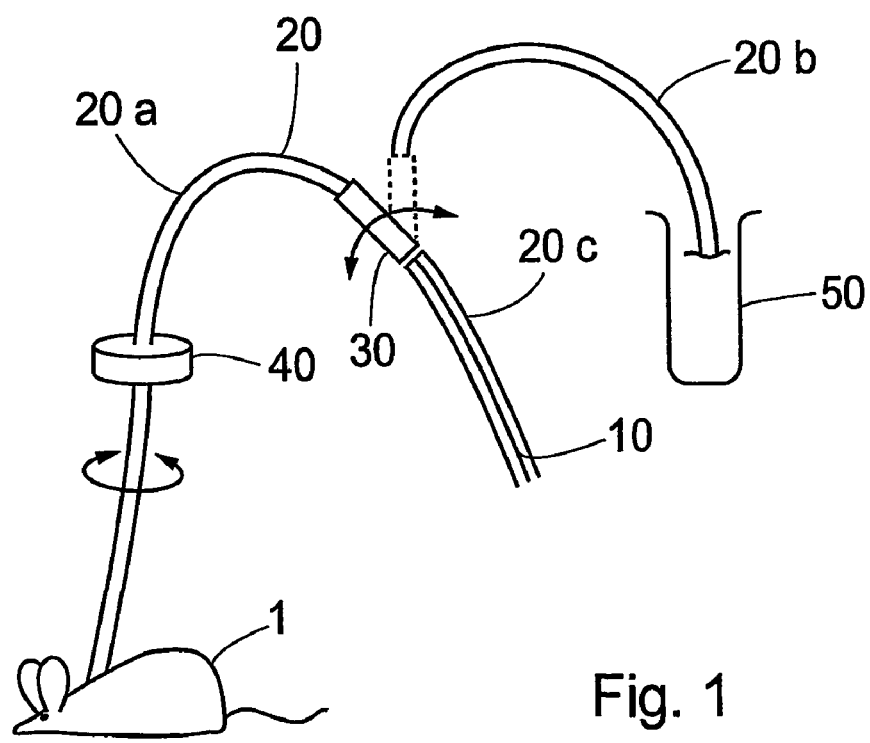
FIG. 1 shows a schematic view of an embodiment of the invention.

FIG. 1 shows schematically a part of an embodiment of the inventive system. A guiding device 20 in the shape of an outer or exterior tubing is configured to lead or guide an elongate specimen collector 10, which in this embodiment is implemented as an inner or interior tubing inside an exterior tubing of the guiding device to a living test object 1. The interior and exterior tubing, respectively, are positioned and configured to be axially movable in relation to each other. The exterior tubing has a first orifice connected to a specimen terminal piece 22 attached to the test object and a second orifice configured for delivering or outputting the content of the specimen collector. In one embodiment of the invention the inner and outer tubing 10 and 20, respectively, are made of a soft material such as Teflon or some other material having a low adhesive surface and a non-reactive surface. In an embodiment of the invention directed to taking a liquid specimen it is particularly important that the inside surface of the cavity operating as a specimen storage in the specimen collector is provided with an inside surface that has a low adhesive capacity. In other words a material to which the specimen does not adhere at all or only to a small extent. The diameter of the tubing 10,20 varies dependent on the type of specimens and the type of living being from which the specimens are to be taken. In any case, in this realisation of the invention the outer diameter of the interior tubing 10 shall be smaller than the inner diameter of the exterior tubing 20. Experimental tests have for example shown that when taking specimens from laboratory animals, such as a rats, suitable dimensions of the exterior tubing is an outer diameter in the range of 3 millimeters (⅛ inch) and an inner diameter in the range of 2 millimeters. The suitable dimensions in a corresponding interior tubing is then an outer diameter in the range of 1.6 millimeters (1/16 inch) and an inner diameter in the range of 0.8 millimeters.

Figure 2:
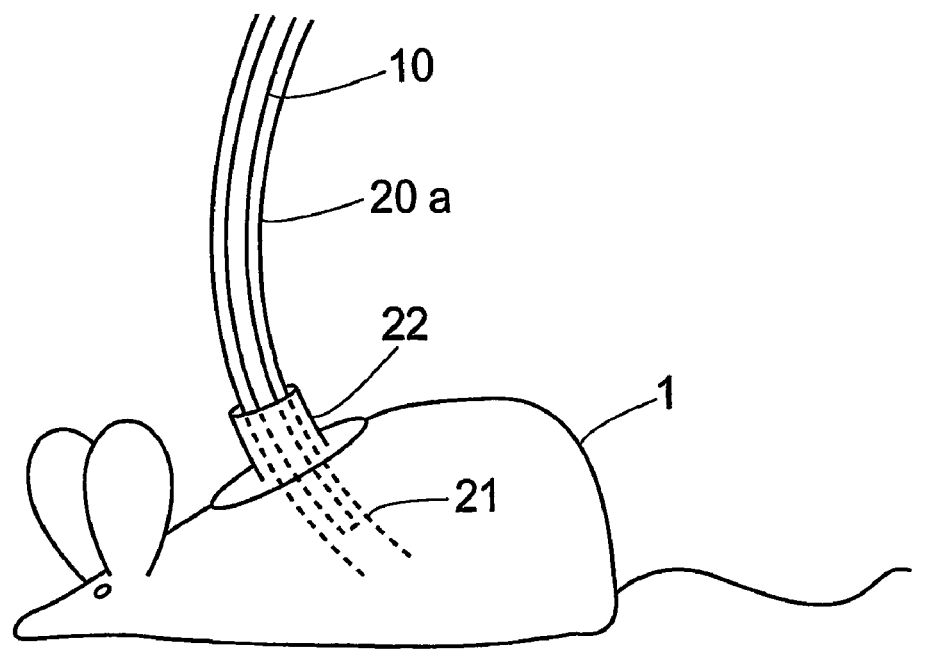
FIG. 2a shows an enlarged view of the distal end of a first tubing branch of a guiding device coupled to a living being in accordance with an embodiment of the invention.
FIG. 2b-2c show a specimen collector before and after it has passed a septum in a specimen terminal.
Figure 2:
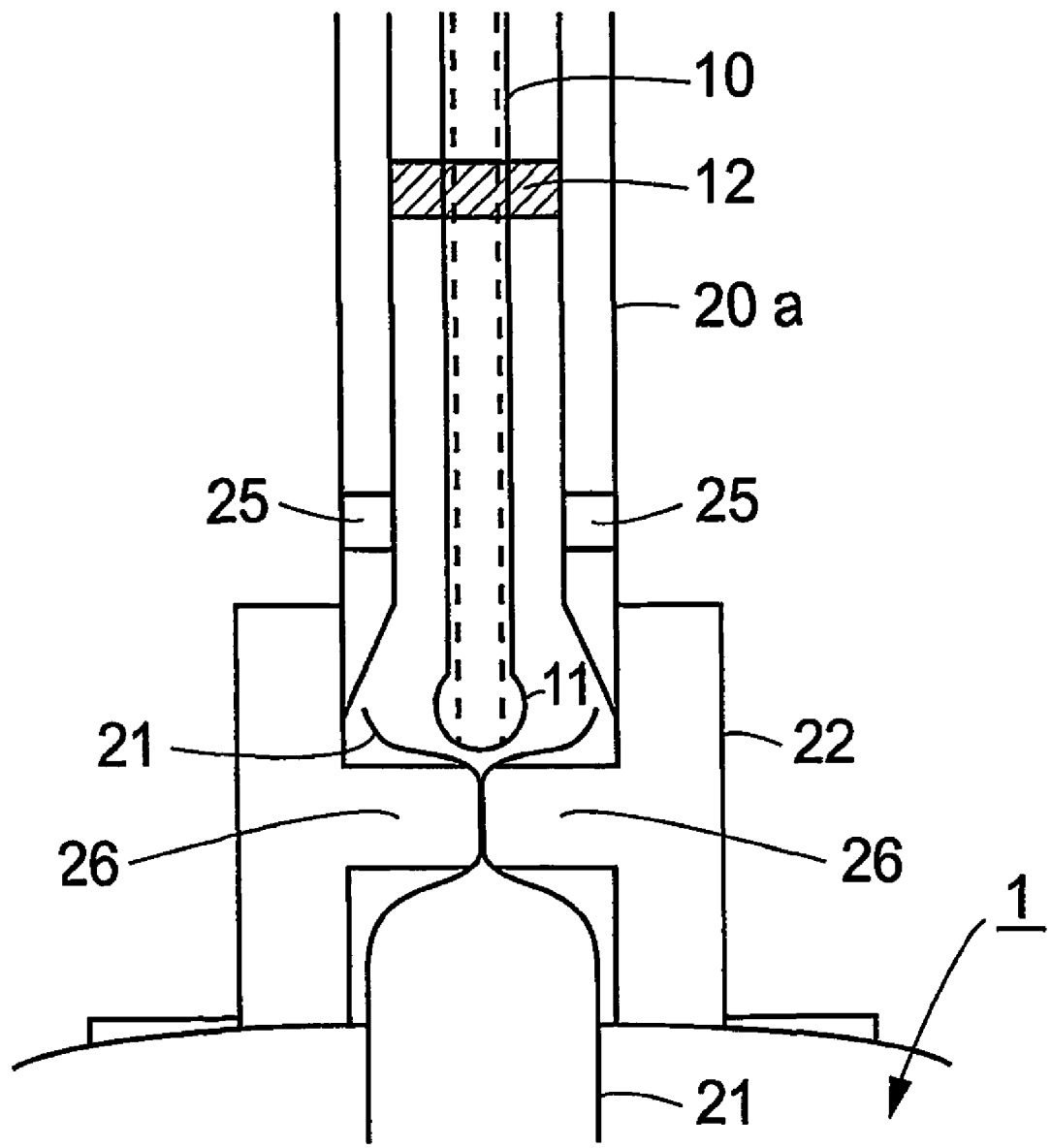
Figure 2:
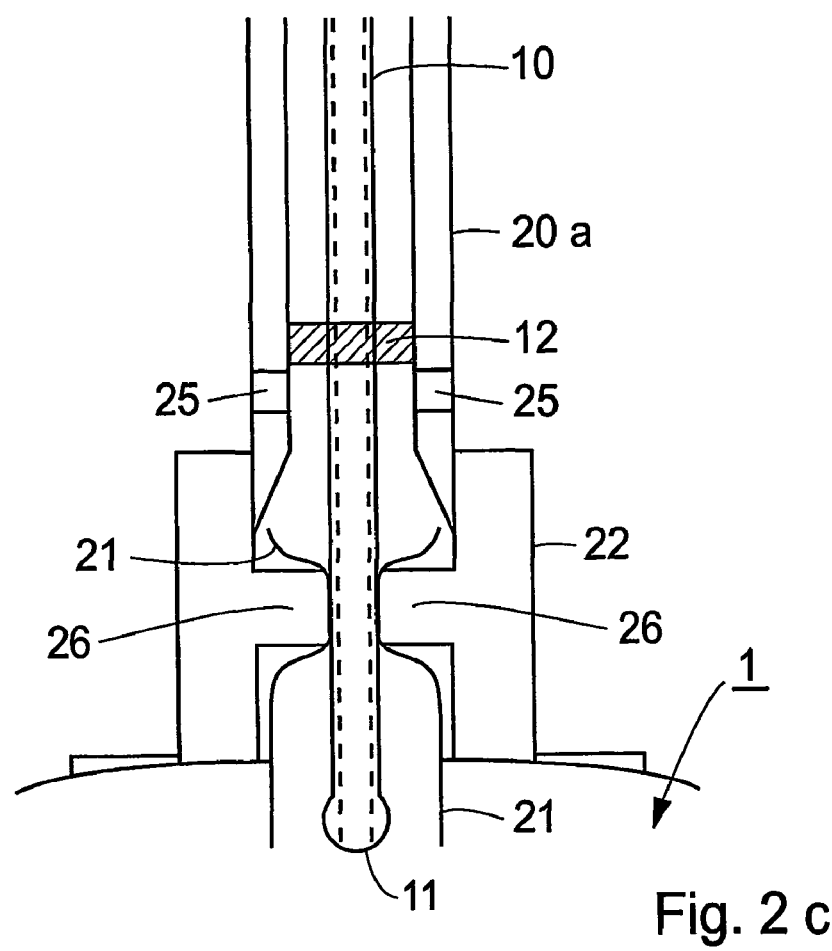

The figure further shows a first tubing branch 20a of the outer tubing 20 coupled to the test object 1 and possibly attached to a swivel 40. The swivel is for example a liquid swivel or some other mechanism, e.g. a radial bearing, that enables freedom of movement of a living test object 1 without being unnecessarily hampered by the guiding device 20. As shown in FIG. 2a, a specimen terminal 22 is attached to the test object 1 and is coupled to the first tubing branch 20a of the outer tubing 20 of the guiding device. Preferably in embodiments applied for living test objects, the specimen terminal 22 is coupled to or comprises a catheter 21 that when in use is inserted into a vessel of the living test object.

Figure 16:
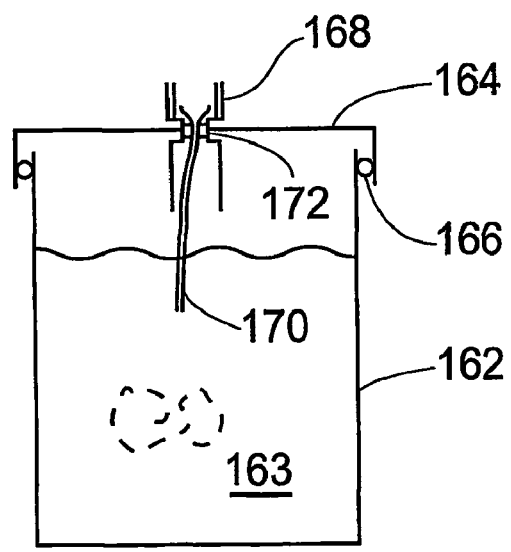
FIG. 16 shows an example of a static test object.

In the case of a non-living test object, the specimen terminal can for example comprise a capillary tube in fluid communication with a monitored or tested fluid. In any case, the specimen terminal is an interface between the sampled fluid, substance or material contained in or constituted by the test object and the guiding device for temporarily connecting to the specimen collector. FIG. 16 shows an example of a static, non-living test object in the shape of a container or vessel 162 containing a fluid 163 from which samples or specimens are to be taken. The shown vessel is provided with a lid 164 and an annular gasket for sealing off the inside of the vessel. A specimen terminal 168 is attached in an orifice of the lid 164 thus operating as an interface for making contact with the fluid in the vessel. The specimen terminal comprises a contraction 172 for sealing and protecting the content between the sampling. In this example the terminal is provided with a capillary tube connected to or encompassed by the contraction 172. A specimen terminal of this kind may also for example be invasively attached to the wall of a pipe or tube for transporting a fluid.

Again referring to FIG. 1, a guiding path points or switch 30, here in the shape of or comprising a tube leader, is coupled to a part of the outer tubing 20c of the guiding device. The guiding path switch 30 is further selectively couplable to the first and second tubing branches 20a and 20c. The function of the guiding path switch 30 is to control the path of the inner tubing of the specimen collector 10 selectively to the path of the first tubing branch 20a, thus leading to the test object, or to the path of the second tubing branch 20b, leading for example to a specimen container or to a waste bin. In a typical operation of a specimen taking cycle, the specimen collector 10 is, after having taken a specimen at the specimen terminal 22, retracted from the first tubing branch 20a to a position proximal the guiding path switch 30. The guiding path switch 30 is actuated to switch the guiding path to the second tubing branch 20b, whereupon the specimen collector is guided down the second tubing branch to its distal end where the specimen is delivered for example to a specimen container. Preferably a rinsing fluid is sucked into the specimen storage of the specimen collector and is thereafter output to a waste bin.

The guiding path switch or tube leader is in one embodiment controlled by an electromagnetic mechanism, but other devices capable of achieving a switch between a first and a second guiding path are of course also conceivable. In one embodiment the tube leader of the switch is made of a soft and flexible material. Furthermore, the elongate tube leader in this embodiment is at its proximal end fastened to or a part of the outer tubing portion 20c and its distal end is actuatable to selectively attain a sealed connection with the proximal ends of the first and second tubing branches 20a, 20b, respectively.

As shown in FIG. 1, the inventive system comprises a specimen delivery station at the distal end of the second guiding path 20b where a specimen container 50, for example one in a series of test tubes for fluid specimen or samples can be docked. At the specimen delivery station the specimen container is preferably movably arranged, for example in a revolving magazine having space for a plurality of containers. Thereby the containers can be moved to and from the delivery station. Correspondingly, the distal end of the second branch 20b of the guiding path can be made movable such that a specimen can be unloaded or output at selected positions e.g. for different receiving containers. As mentioned before, the system may also comprise a rinsing station (not shown) or a waste container (not shown) that is configured to be positioned at the distal end of the second branch 20b. Preferably the distal end of the branch 20b and the waste container are movable in relation to each other, by movement of the branch 20b or by movement of the waste bin.

Specimen Terminal

FIG. 2a shows an enlarged and schematic view of how the first tubing branch 20a of the outer tubing 20 and a fastening device or a specimen terminal 22 are coupled to a living test object 1 via a catheter 21 in an embodiment of the invention. In the example of taking blood specimens, the distal end of a catheter 21 coupled to or possibly comprised in the specimen terminal 21 is inserted in a blood vessel, e.g. an artery of the living test object. The proximal end of the catheter is coupled to the distal end of the first tubing branch 20a by means of a coupling mechanism comprised in the specimen terminal 22. The specimen terminal is configured for positioning the catheter output at the living test object, for attaching the guiding device to the test object and for providing an interface between the test object and the specimen collector. Preferably the specimen terminal 22 is springy, resiliently or elastically attached to the living test object 1 in order to decrease or minimise the impact of the taking of specimens. That is, the specimen terminal 22 is devised to reduce the or even out the pressure forces, the traction forces or the movements that are caused in connection with the taking of specimens, the movement of the specimen collector and the actuation of the guiding path switch. In the shown embodiment the specimen terminal 22 is provided with a flange designed with a suitable area against the test object 1 for the purpose of reducing pressure forces. Preferably the material is also resilient for example Dacron or the like.

FIG. 2b and FIG. 2c show an embodiment of the specimen terminal 22 engaged with the specimen collector 10. The shown specimen terminal 22 comprises a contraction 26 in the path of the specimen collector 10 inside the specimen terminal 22 and encompassing the proximal end of a catheter 21. The contraction is made compliant or resilient to squeeze in a springy or elastic manner the catheter 21 to be sealed by means of the contraction. This arrangement is made to prevent e.g. arterial blood from the living test object 1 to leak out through the catheter between the specimen taking occasions.

Figure 5:
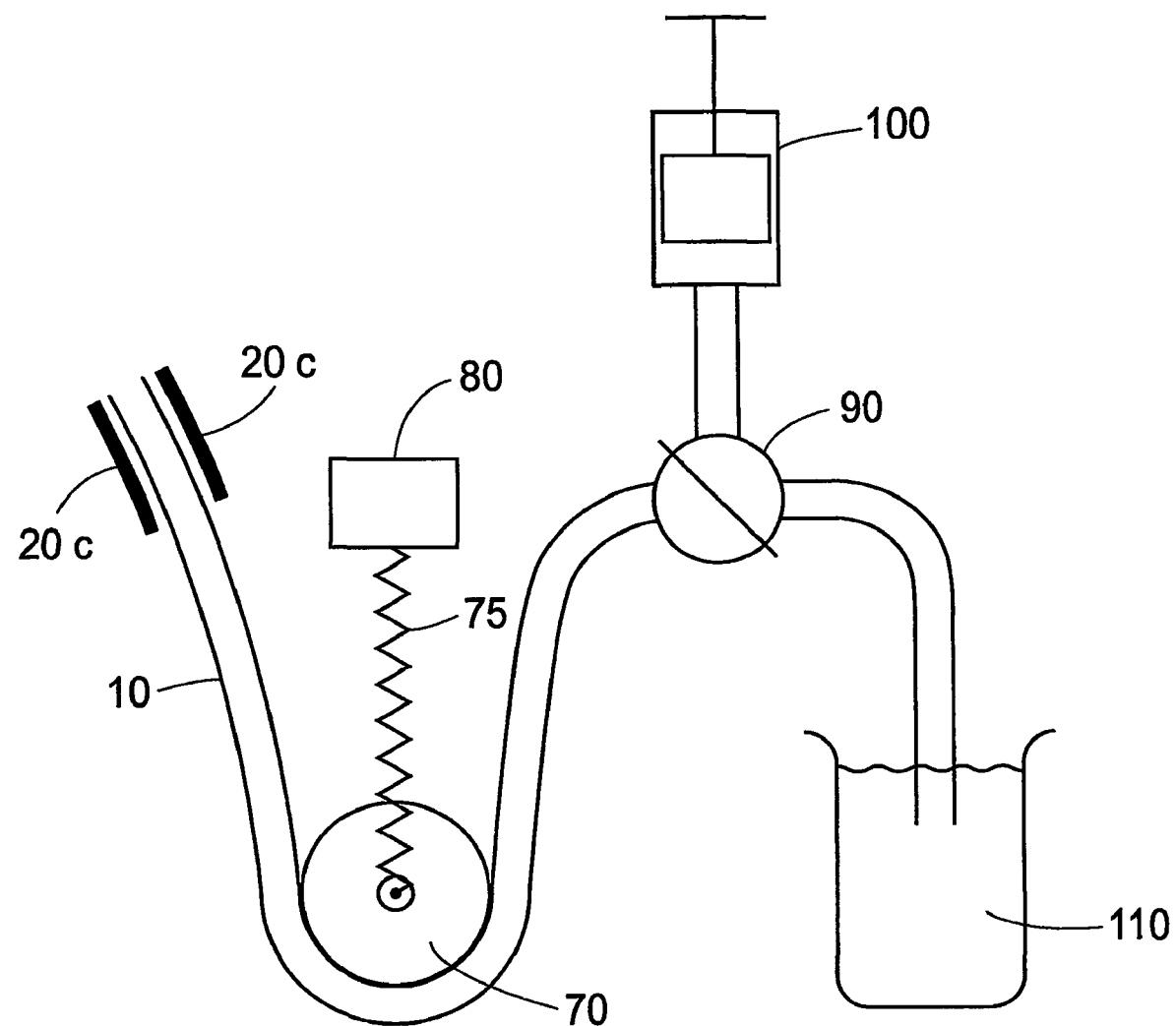
FIG. 5a-5b show schematically the function of a spring suspended device for controlling the movement of a guiding device in accordance with embodiments of the invention.
Figure 5:
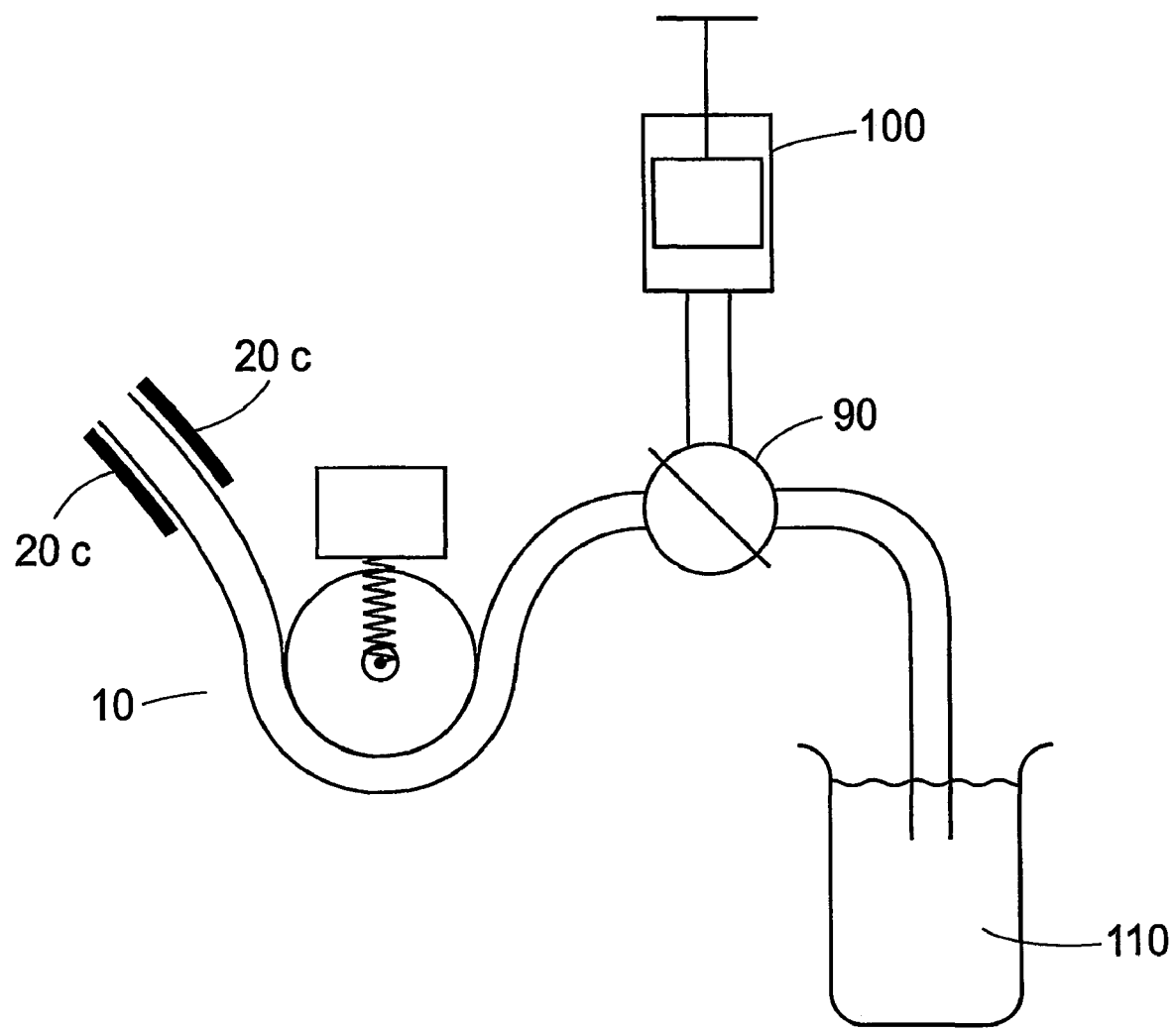

A first branch 20b of the outer tubing 20 is fastened to the specimen terminal 22 and is preferably provided with at least one passage or perforation 25, or some other device with openings for equalising pressure and insuction of for example air or a separation medium. In the first tubing branch 20b said perforation 25 enables pressure equalising in the area between the contraction 26 of the specimen terminal 22 and the distal part of the inner tubing or a lead of the specimen collector 10 when it is moved towards the living test object 1. In the course of this movement air or fluid, e.g. blood, that is situated proximal the contraction 26 and distal a gasket 12 attached to inner tubing or lead can escape through the perforation 25. The perforation also enables insuction of for example air into the lumen of the inner tubing of the specimen collector 10 at its distal end. An insuction of air or another separation medium is preferably carried out before taking a specimen in order to separate the specimen from a solution or substance in the lumen of the specimen collector 10. Insuction of a separation medium is preferably also carried out also after taking the specimen in order to avoid contaminating the inside of the outer tubing 20 when the inner tubing 10 is retracted and moved in the outer tubing. Insuction of a separation medium and a specimen into the lumen or cavity of the inner tubing is in one embodiment carried out by means of a pumping device 100, for example a piston pump, arranged at the proximal end of the inner tubing (Cf FIG. 5a and FIG. 5b).

In the embodiment shown in FIGS. 2a and 2b the specimen terminal 22 is a tube like device comprising a contraction 26 preferably in the shape of a septum, for example a silicone septum having a cut or punched opening. The catheter 21 is in a preferred embodiment closed by means of the septum and the septum is opened and penetrated by the specimen collector when the specimen collector is lead forward into the catheter. In this position the septum seals against the inner tubing of the specimen collector. On the distal side of the septum, the distal end of the specimen collector is in a direct contact with the sampled fluid and a specimen is extracted or sucked from the catheter into the lumen of the inner tubing. After insuction of a specimen the specimen collector 10 is retracted past the septum, which resumes its original shape or position.

The need for a swivel for following the movements of the living test object is avoided by seeing to it that the distal end of the specimen collector 10 is in contact with components that are attached to the living test object only during the short period of time when the taking of a specimen is carried out.

Specimen Collector

Figure 3:
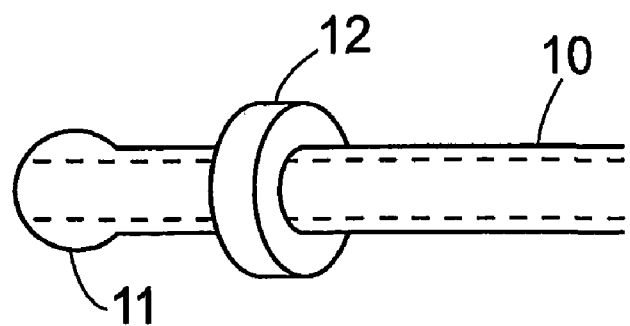
FIG. 3 shows an embodiment of a specimen collector at its distal end.

FIG. 3 (Cf. also FIG. 2b-2c) shows an example of the design of a specimen collector 10. The specimen collector 10 is preferably made relatively soft and bendable as an elongate inner or interior tubing or lead having a lumen extending from the distal end to a proximal position. In the shown embodiment the distal end of the specimen collector 10 is provided with a rounded soft distal widening part 11 or specimen collector head, by means of which the opening of the contraction 26 or septum in the specimen terminal is dilated and penetrated. The shown distal widening part 11 has the shape of a ball, but can also have another geometric form that is narrowing in its distal and proximal directions. Preferably the outer shape of the distal part 11 has a mantle surface having a diameter that in its distal direction first increases to a largest diameter adapted to penetrate the septum and then decreases. In one embodiment, the distal part 11 has a length in the range of about 5 to 8 millimeters. The distal part 11 is further provided with a passage or lumen that is in communicative connection with the lumen of the inner tubing or the lead of the specimen collector 10. A taken specimen thus passes through the distal part 11 to the lumen of the inner tubing. In one embodiment the inner tubing as well as the distal part is made of Teflon, and in another embodiment the inner tubing is made of Teflon and the distal part 11 is made of PEEK (Poly Eten Eten Keton). The distal part is preferably made in a harder material than that of the inner tubing, in order to be more apt to open or penetrate the contraction or septum 26.

Figure 4:
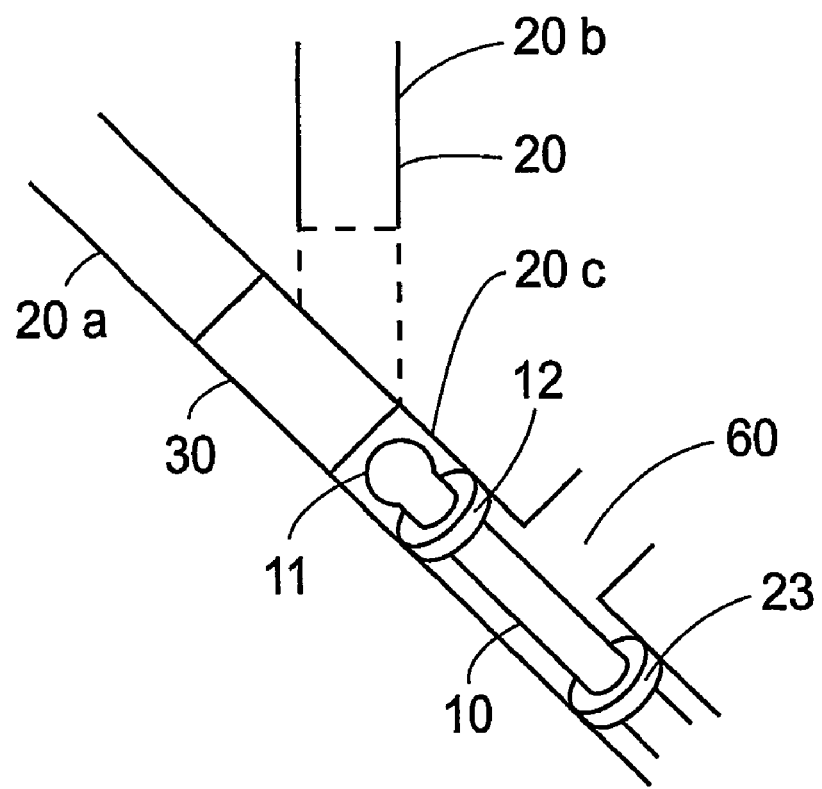
FIG. 4 shows an embodiment of a specimen collector arranged in the guiding device.

The shown inner tubing further comprises a first gasket or a flange 12 that is arranged at the outside of the inner tubing or lead of the specimen collector 10. The gasket is in this embodiment devised to achieve a sealing between the outside of the inner tubing or lead and the inside of the outer tubing of the guiding device 20, as shown in FIG. 4. In one embodiment of the specimen collector 10 the inner tubing or lead is connected to the distal part 11 in the first gasket 12, but they can of course also be connected somewhere else or even be manufactured in one piece as an integrated unit. Furthermore, a second gasket 23 is arranged at the inside of the outer tubing and is also arranged to seal between the outside of the inner tubing or lead of the specimen collector 10 and the inside of the outer tubing 20. In this embodiment the sealing that is achieved by means of the two gaskets 12,23 is used for moving the inner tubing or lead of the specimen collector 10 forwards in the outer tubing 20, i.e. in the direction of the living test object down the first branch 20a. Alternatively, the inner tubing or lead is moved forwards in the direction of the specimen container down the second branch 20b. This is preferably carried out pneumatically by supplying compressed air through a first compressed air inlet 60, arranged at the outer tubing 20 between the gaskets 12,23. The air exerts a pressure on the gaskets, and since the second gasket 23 is fastened to the inside of the outer tubing 20 the air pressure will act on the first gasket 12 that is fastened to the outside of the inner tubing. The inner tubing 10 will thereby be moved away from the air inlet 60 down the first or second branch 20a, 20b dependent on the position of the guiding branch switch 30.

Displacement of Specimen Collector

In FIG. 5a and FIG. 5b it is shown how the inner tubing or lead of the specimen collector 10 is connected to a container 110 for a rinsing fluid, preferably a heparinised sodium chloride solution. In this embodiment the inner tubing or lead runs or slides around a pulley 70, which possibly is engaged with a driving means 80, e.g. a motor, via a spring element 75. Furthermore a regulator means 90 preferably a valve, for example a pump valve, is mounted to the lumen of the specimen collector 10, preferably at its proximal end. When the inner tubing or lead of the specimen collector is moved by means of applied pressurised air in the distal direction of the outer tubing of the guiding device 20c, i.e. down the first branch towards the test object or down the second branch towards the specimen container, the inner tubing or lead will compress the spring element 75 against the fixedly arranged motor 80, as shown in FIG. 5b. When the inner tubing or lead shall be retracted from a distally advanced position, the supply of pressurised air is stopped and the motor 80 is actuated to press out the spring element 75 to an extended position, whereupon the inner tubing or lead is retracted to a more proximal position as shown in FIG. 5a.

In one embodiment lacking the motor 80, the spring element 75 is fastened to a fixed object. The spring element 75 is in a forward movement of the specimen collector 10 compressed by the air pressure force that is exerted on the gasket 12. When retracting the specimen collector 10 from a distally advanced position the air pressure supply is stopped, whereupon the spring element 75 expands and displaces the pulley 70 and thus pulls the specimen collector out of the outer tubing 20c of the guiding device.

Figure 6:
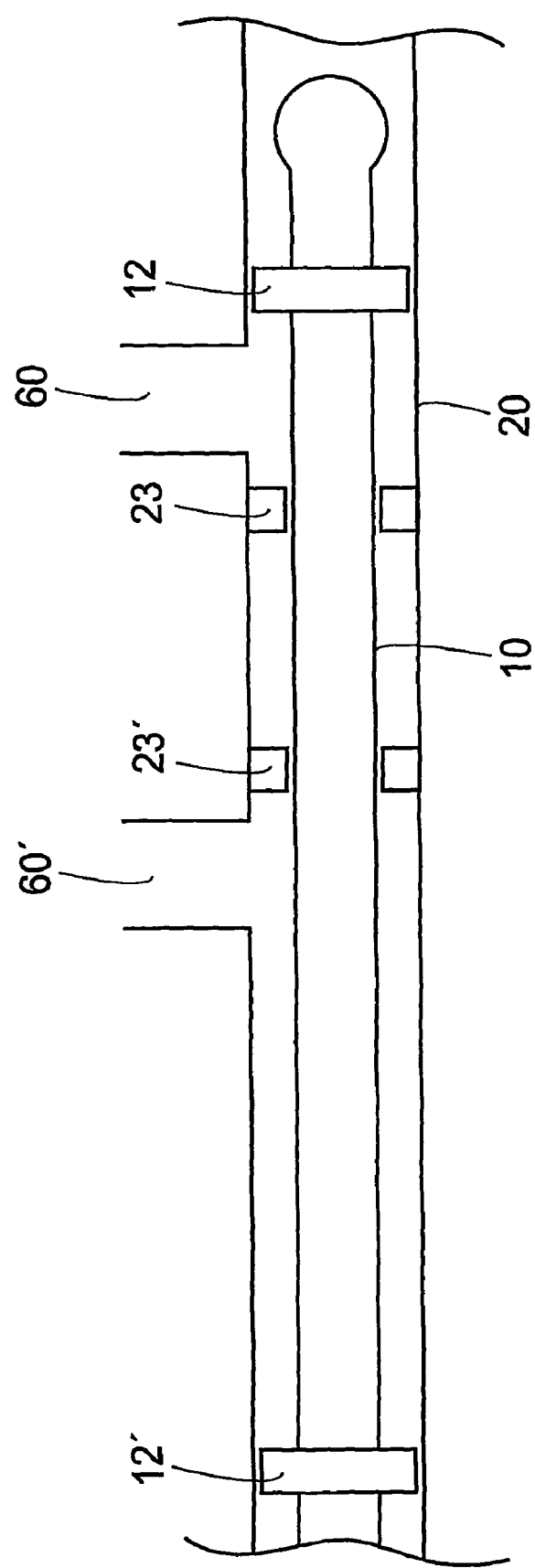
FIG. 6 shows schematically the function of a pneumatic device for controlling the movement of a guiding device in accordance with embodiments of the invention.

FIG. 6 shows schematically an embodiment of the invention, in which the specimen collector is displaced pneumatically in the forward as well as the backward directions past the guiding path switch. For this purpose there is a second compressed air inlet 60' in the outer tubing, and a third gasket or flange 12' arranged on the inner tubing or lead of the specimen collector 10. In one variety there is even a fourth gasket or flange 23' arranged on the inside of the outer tubing 20. It should be understood that the gaskets or flanges 12,12',23,23' are drawn in the figure with an exaggerated distance to the surface it seals against for purpose of showing the respective position and mounting. In order to drive the inner tubing or lead of the specimen collector 10 in a distal direction, compressed air is supplied as described above. When the first air 60 inlet is closed and compressed air instead is supplied through the second air inlet 60', a pressure force is exerted on the third gasket 12' and the specimen collector is driven backwards and can be retracted past the guiding path switch 30. The guiding path switch can be actuated to engage a selected branch to the guiding path and again compressed air can be supplied through the first air inlet 60, whereupon the specimen collector is driven forwards down the selected branch path to a selected position dependent. The position to which the specimen collector is driven is controllable dependent on the time and amount of supplied compressed air.

The gaskets or flanges 12,12',23,23' are preferably made in Teflon or some other material having a low friction in relation to the respective tube surface, in order to facilitate a displacement of the specimen collector inside the tubing of the guiding device.

In a not shown embodiment of the invention there is an indicator arranged at the guiding device or at the specimen collector configured to indicate the relative or absolute position of the specimen collector in the guiding device. In one variety a magnetic strip is mounted along the inner tubing or lead of the specimen collector, for example at its outside surface. The magnetic strip comprises a series of magnetic equidistantly positioned north and south poles. A magnetic reader or detector is mounted at the outer tubing of the guiding device, by means of which the position of the inner tubing or lead can be determined.

Method for Taking Specimen

Figure 7:
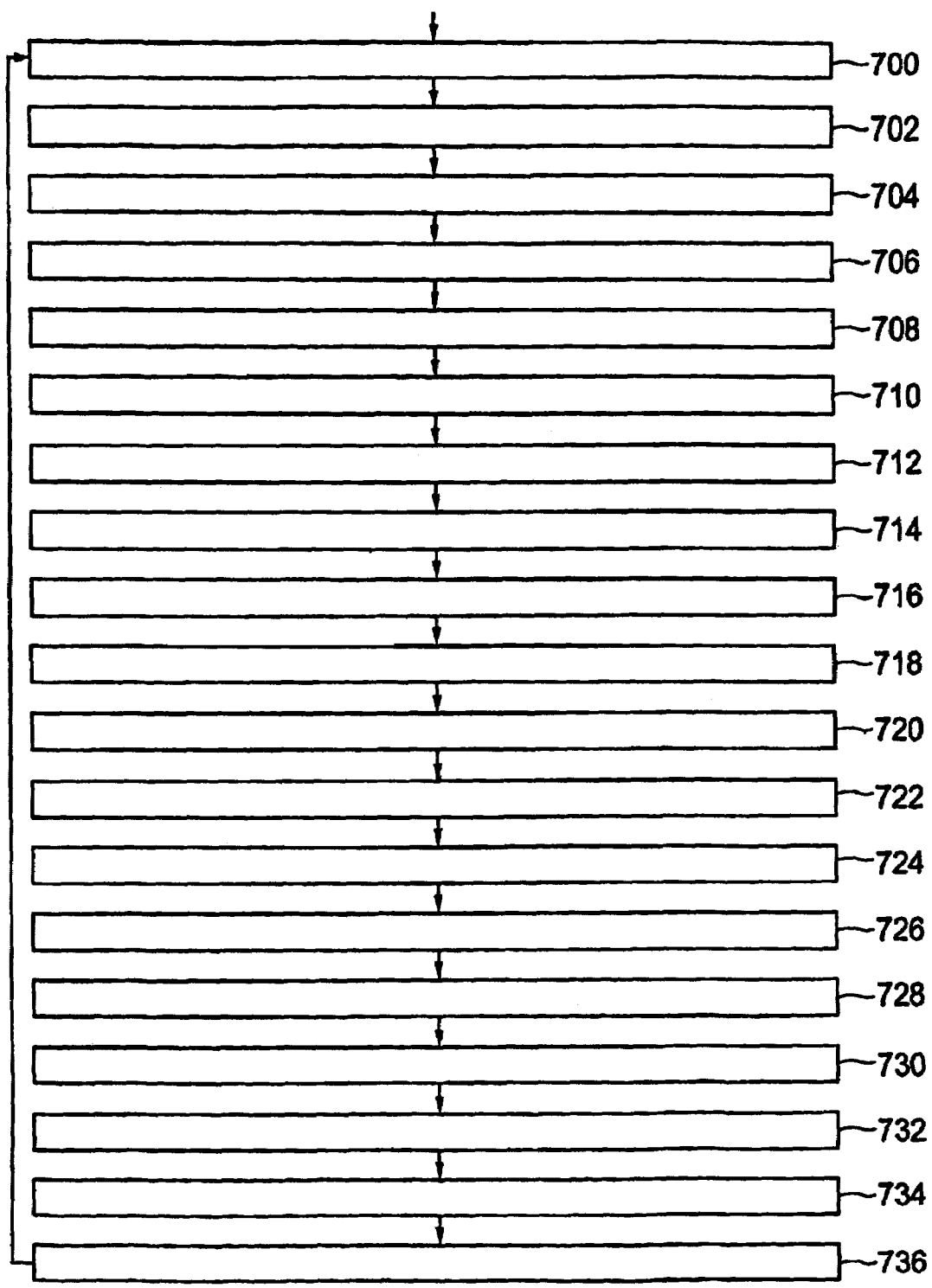
FIG. 7 shows a flow chart of method steps in an embodiment of the invention.

FIG. 7 (also Cf. FIG. 1-6) shows a flow chart of the inventive method steps for taking specimens by means of an exemplifying embodiment of the invention. The shown embodiment comprises the following steps:

| | |
|---|---|
| 700 | Leading the inner tubing of the specimen collector 10 through the first tubing branch 20a of the outer tubing 20 of the guiding device to the specimen terminal 22 at a living test object 1. |
| 702 | Insuction of about 10 microlitres of air through the perforation 25 of the outer tubing 20 into the lumen of the inner tubing containing a sterile rinsing fluid, preferably a heparin treated sodium chloride solution. |
| 704 | Leading the inner tubing 10 forward in a distal direction past the contraction 26 and into the catheter 21, said catheter 21 being arranged in e.g. an artery in the living test object 1. |
| 706 | Insuction and thereby extracting of a fluid specimen, e.g. a blood sample, amounting to a selectable volume from the living test object 1 into the lumen of the inner tubing. |
| 708 | Leading and thereby retracting the inner tubing backwards in a proximal direction past the resilient contraction 26 in the specimen terminal 22. |
| 710 | Insuction of more air into the distal part of the lumen of the inner tubing for the purpose of preventing contamination of the inside of the outer tubing be the specimen. |
| 712 | Leading and thereby retracting the inner tubing through the first branch of the outer tubing and past the guiding path switch 30. |
| 714 | Actuating the guiding path switch 30 such that the second branch of the outer tubing leading to a specimen container is an open guiding path. |
| 716 | Leading the inner tubing through the second branch 20b to the specimen container 50 at the distal opening of said second branch 20b. |
| 718 | Delivering the specimen by pumping out the specimen into the specimen container 50. |
| 720 | Exchanging the specimen container against a waste container for waste fluid at the distal end of the second branch 20b. |
| 722 | Actuating the pump valve 90 such that connection between the rinsing fluid container 110 and the pumping device 100 is open. |
| 724 | Insuction, by means of the pumping device 100, of a rinsing fluid from the container 110. |
| 726 | Actuating the pump valve 90 such that the connection between the inner tubing 10 and the pumping device 100 is open. |
| 728 | Pumping the rinsing fluid through the lumen of the inner tubing to its distal end and delivering said fluid to the waste container at the distal opening of said second branch 20b. |
| 730 | Exchanging the waste container against a specimen container 50 at the distal opening of the second branch 20b. |
| 732 | Leading back thereby retracting the inner tubing past the guiding path switch 30. |
| 734 | Actuating the guiding path switch such that the first branch 20a is open. |
| 736 | Repeating the specimen taking procedure in accordance with the steps 700–734. It should be understood that the above described method steps can be performed in other suitable orders than that of the previous description. |

Further Embodiments of System Components

Figure 8A:
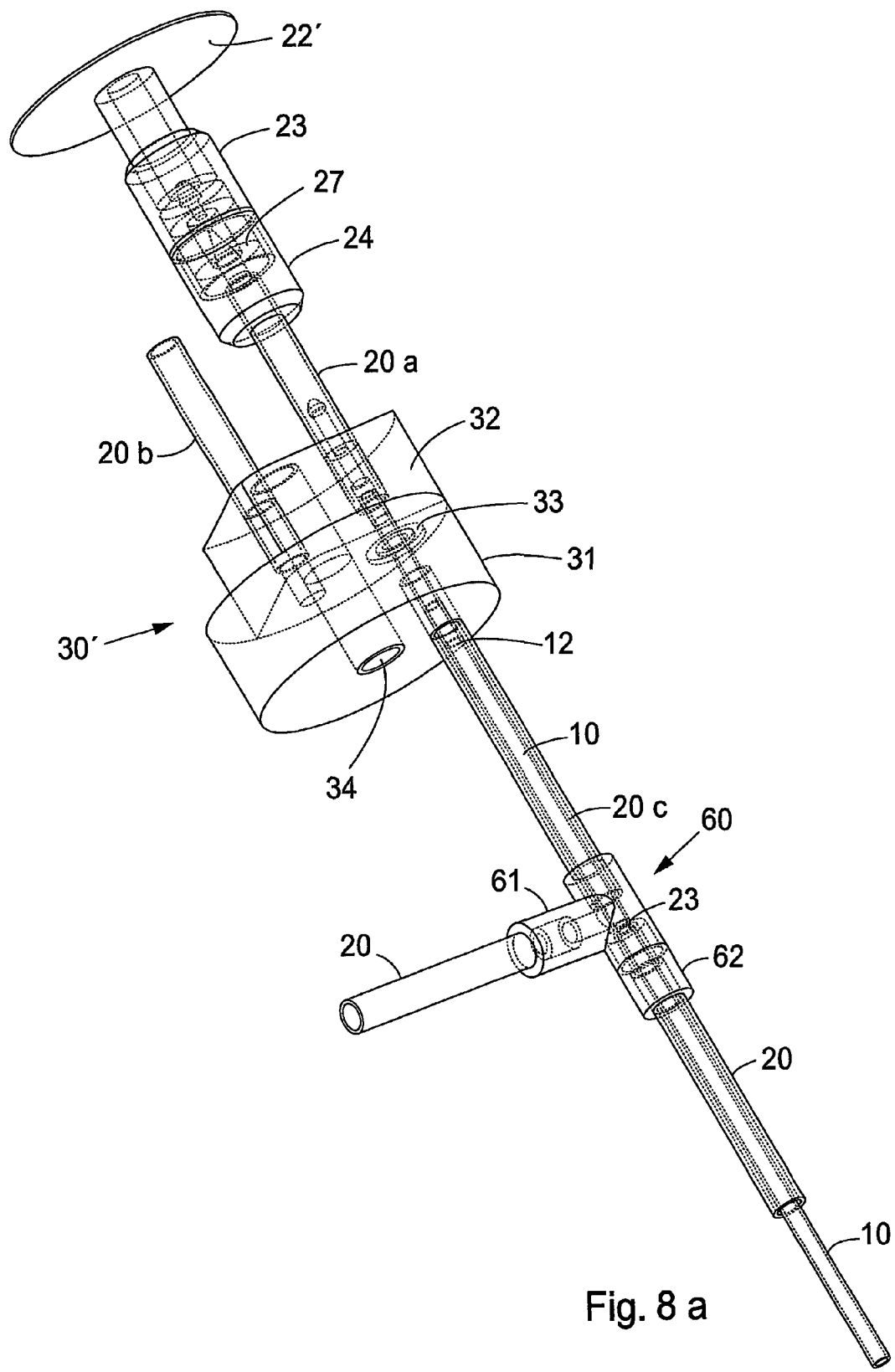
FIG. 8a-14 show schematically functional details of embodiments of the invention.
Figure 8:
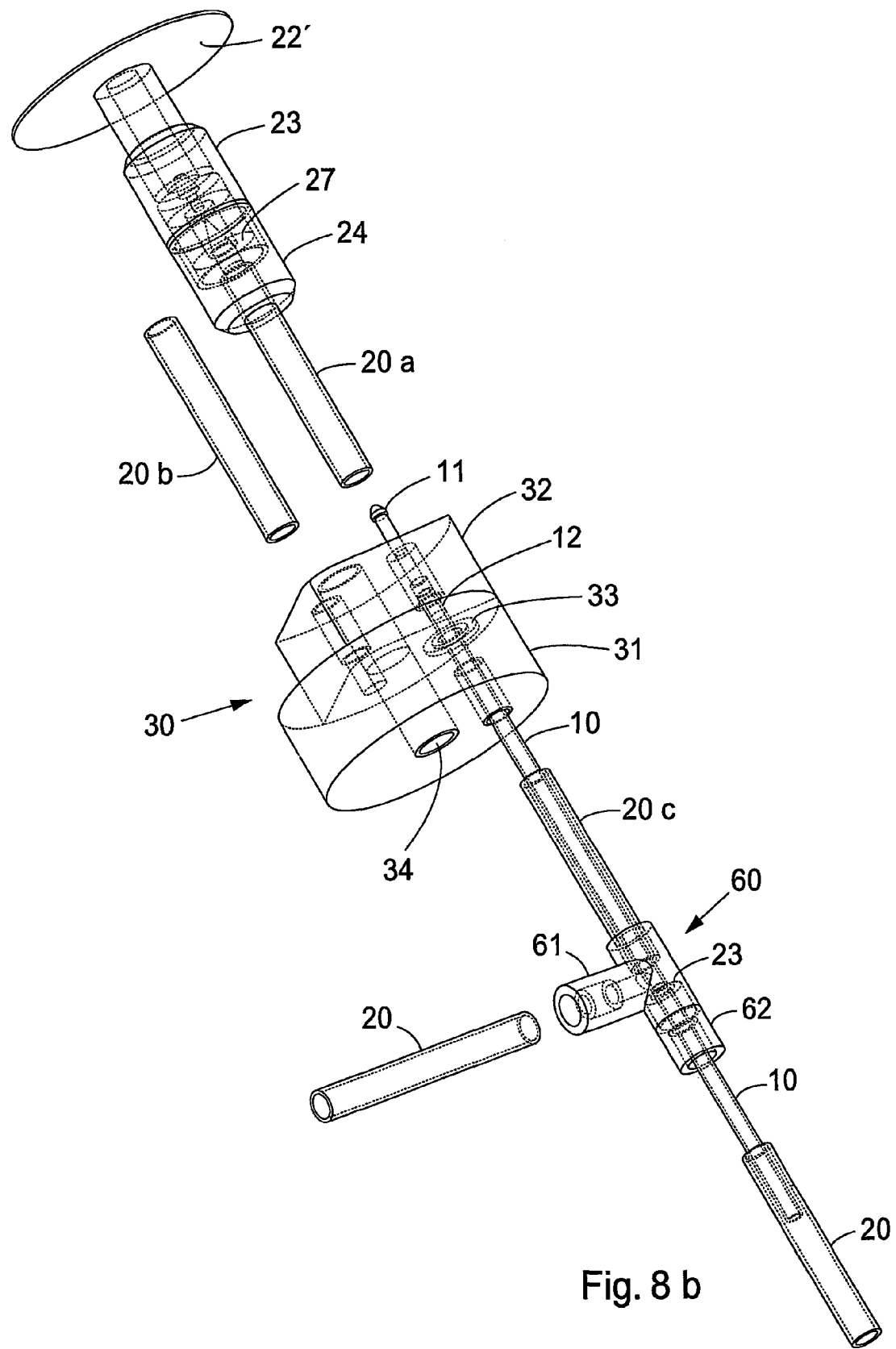
Figure 9:
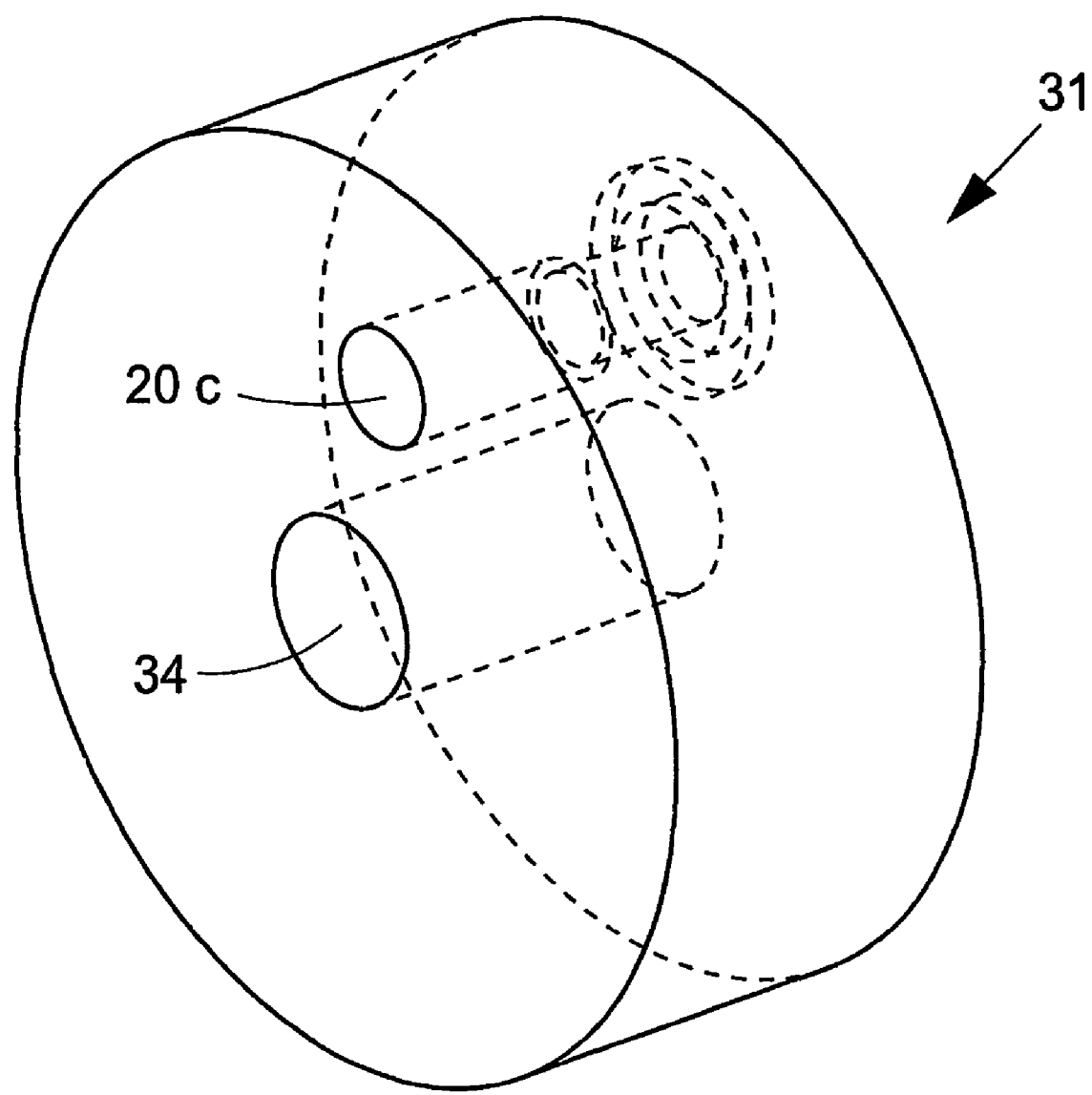
Figure 9:
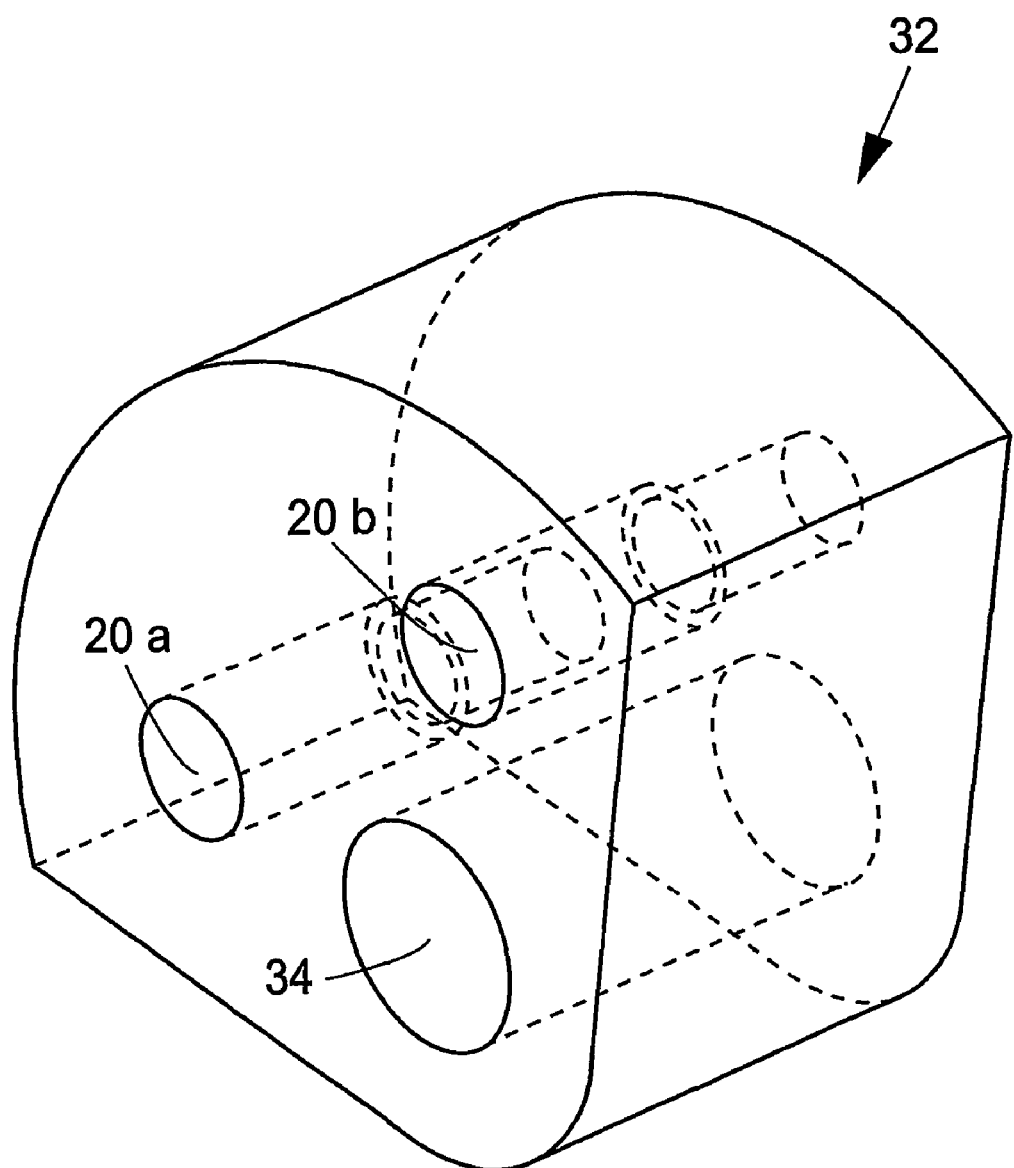

FIG. 8a and FIG. 8b shows a detailed drawing of an embodiment of parts and components of the inventive system. The FIGS. 9-14 show exemplifying drawings of separate components of this embodiment. Components corresponding to those described in connection with the drawings in FIG. 1-4 are for the sake simplicity denoted with the same reference numbers in most of the drawings. The embodiment is shown in an assembled view in FIG. 8a and in an exploded view in FIG. 8b.

The specimen collector 10 is designed as an interior tube placed inside the guiding device 20 that has the shape of an exterior tube. The guiding path switch 30' comprises a stator part 31 and a rotor part 32 as well as a not shown axis to be mounted in the coaxial openings 34 of the stator part and the rotor part. The proximal part of the guiding tube 20c leads through an opening in the stator part 34, whereas the first and the second tube branches 20a and 20b leads through respective openings in the rotor part 32. The axis drives the rotor part 32 of the guiding path switch 30' to rotate relative the stator part 34 in order to selectively position the proximal part 20c of the guiding tube in a coaxial position with the respective tube branches 20*a* and 20*b*. Thereby a selected branch path is opened or closed. A closer view of the stator part 31 is show in FIG. 9*a* and a rotor part 32 is shown in FIG. 9*b*.

A annular gasket 33, e.g. an O-ring, is preferably mounted at the distal opening of the tube part 20*c* in the stator part 32, in order to seal the connection between the tube part 20*c* and the respective tube branch 20*a* and 20*b*. As an alternative gaskets or some other sealing mechanism can be arranged on the rotor part 32 at the connection with the first and second branch 20*a*,20*b*, respectively.

Figure 10:
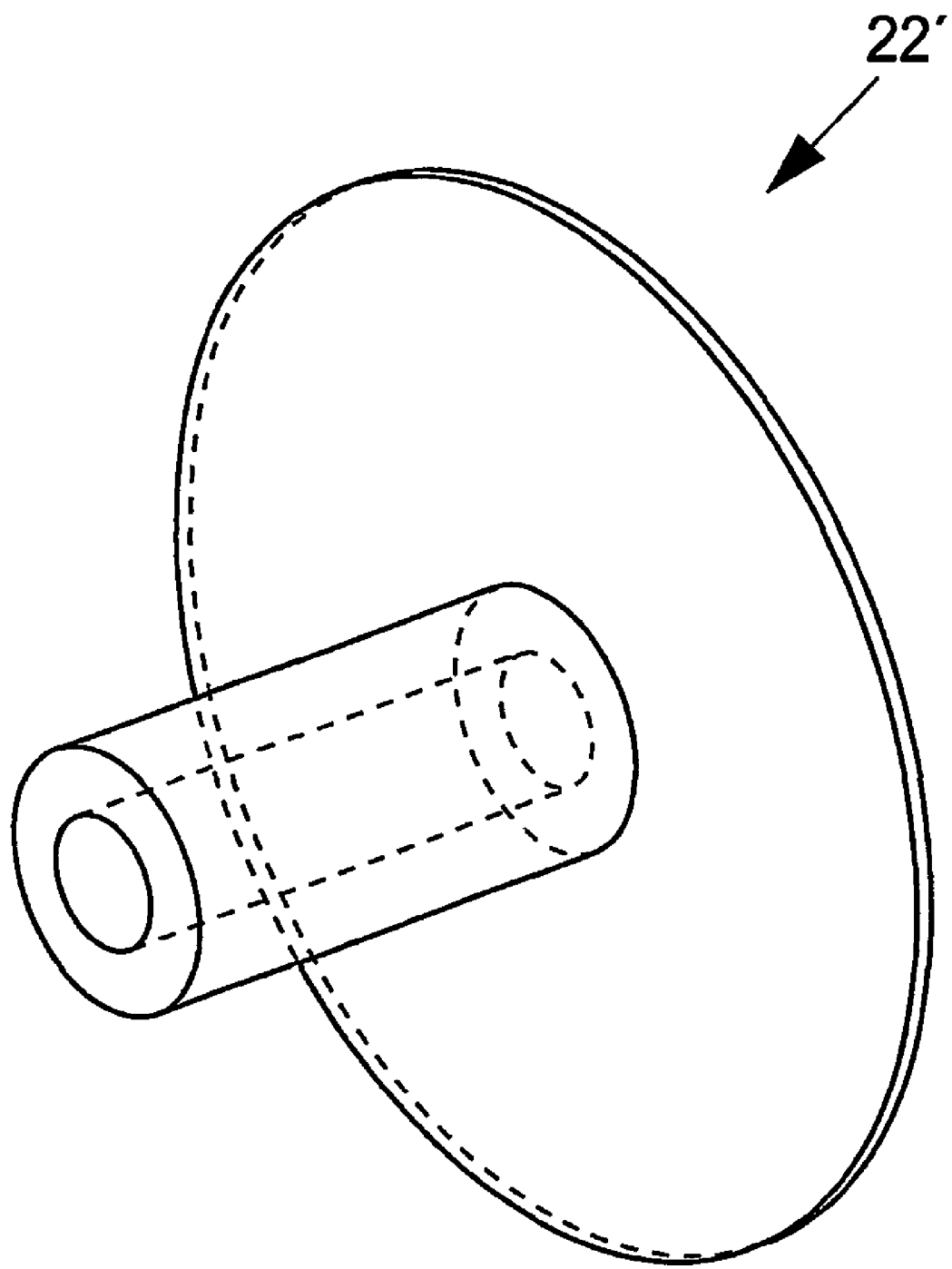
Figure 11:
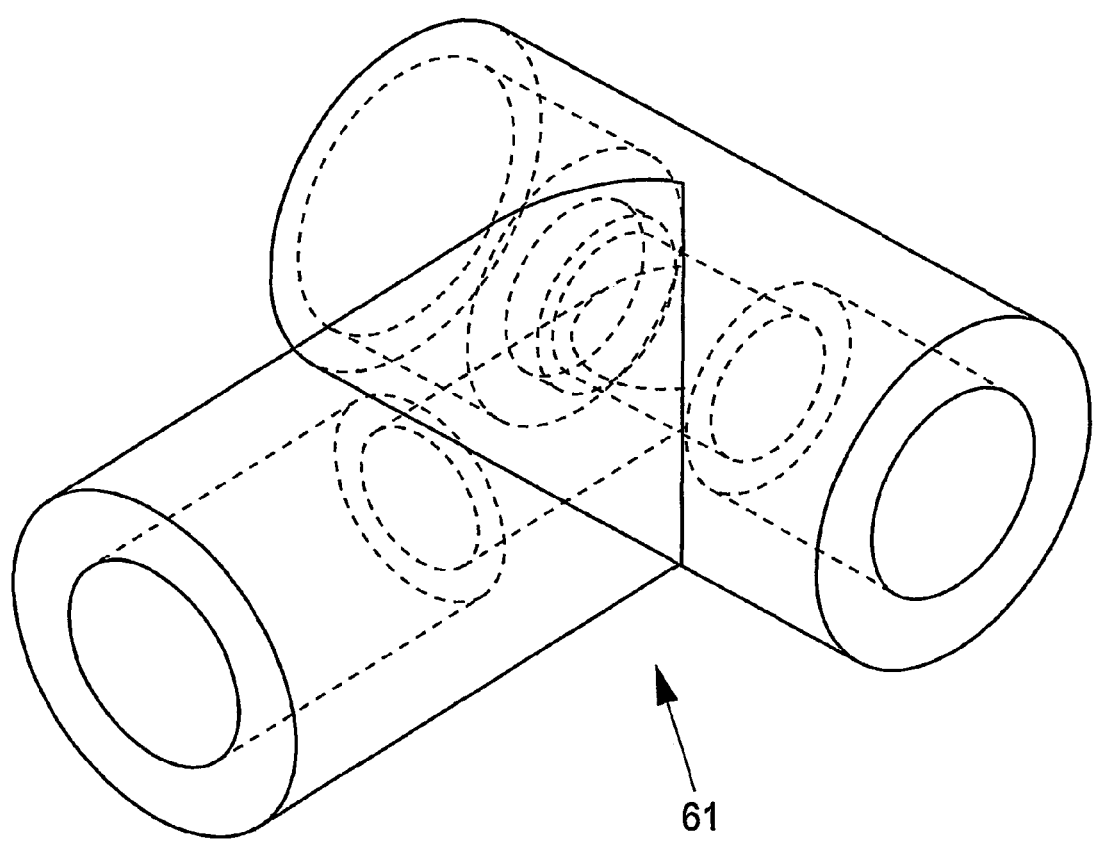
Figure 11:
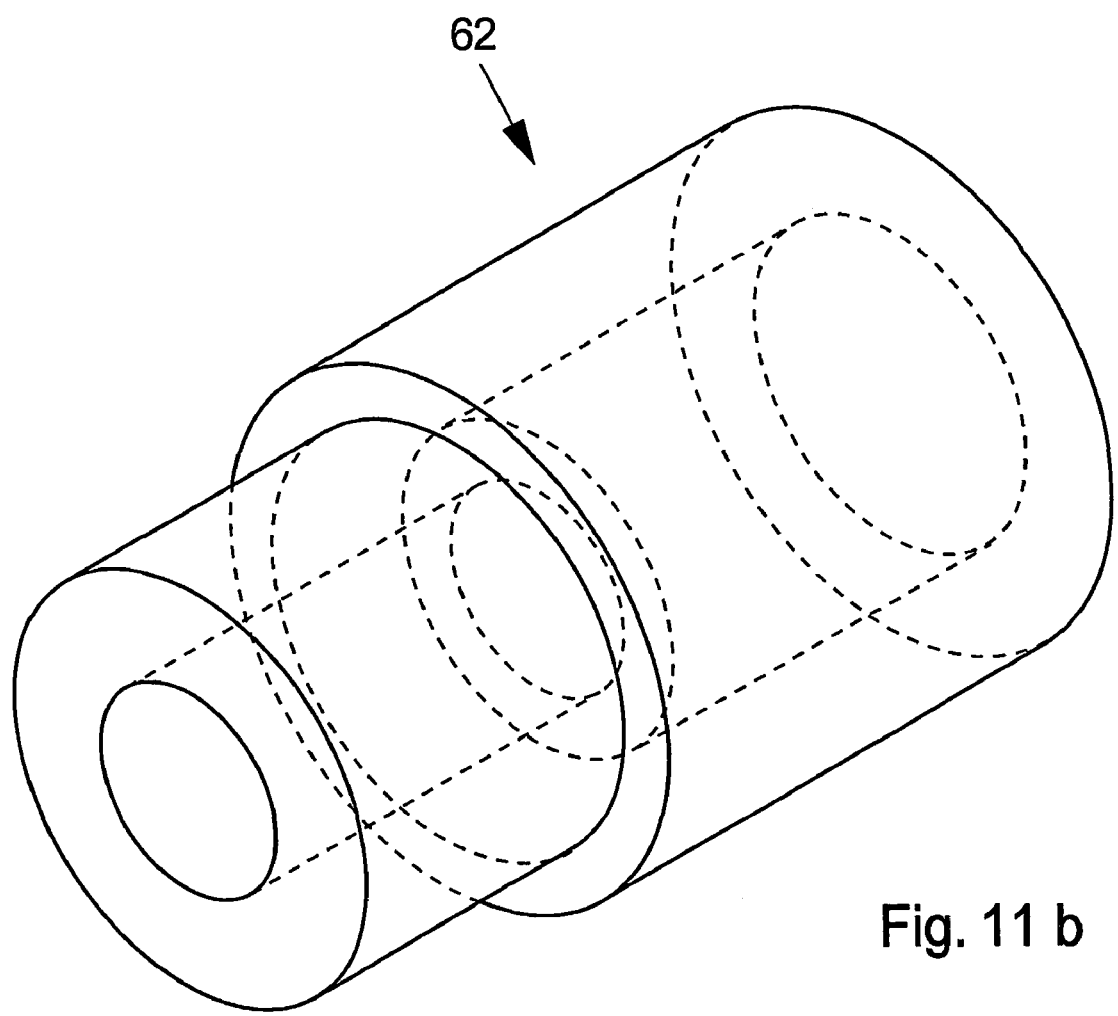
Figure 12:
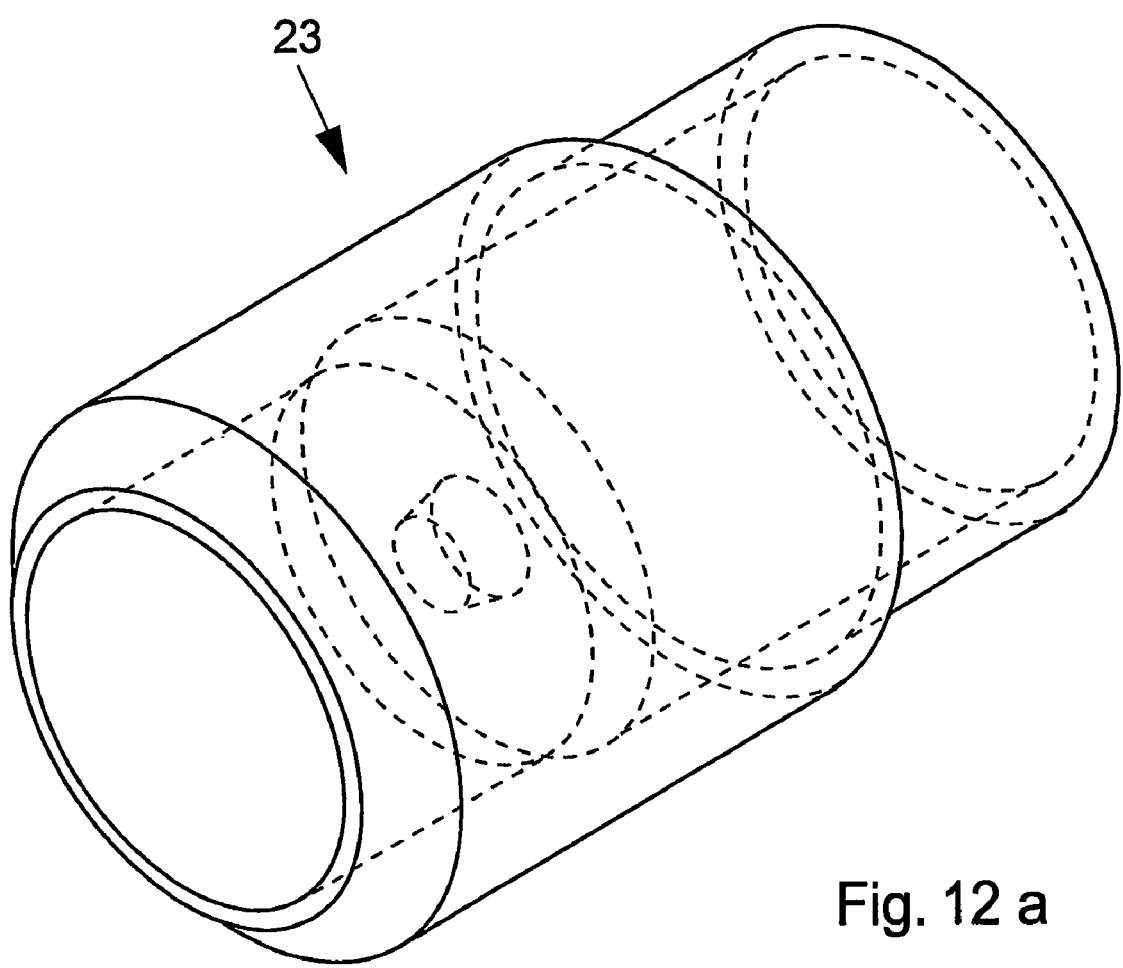
Figure 12:
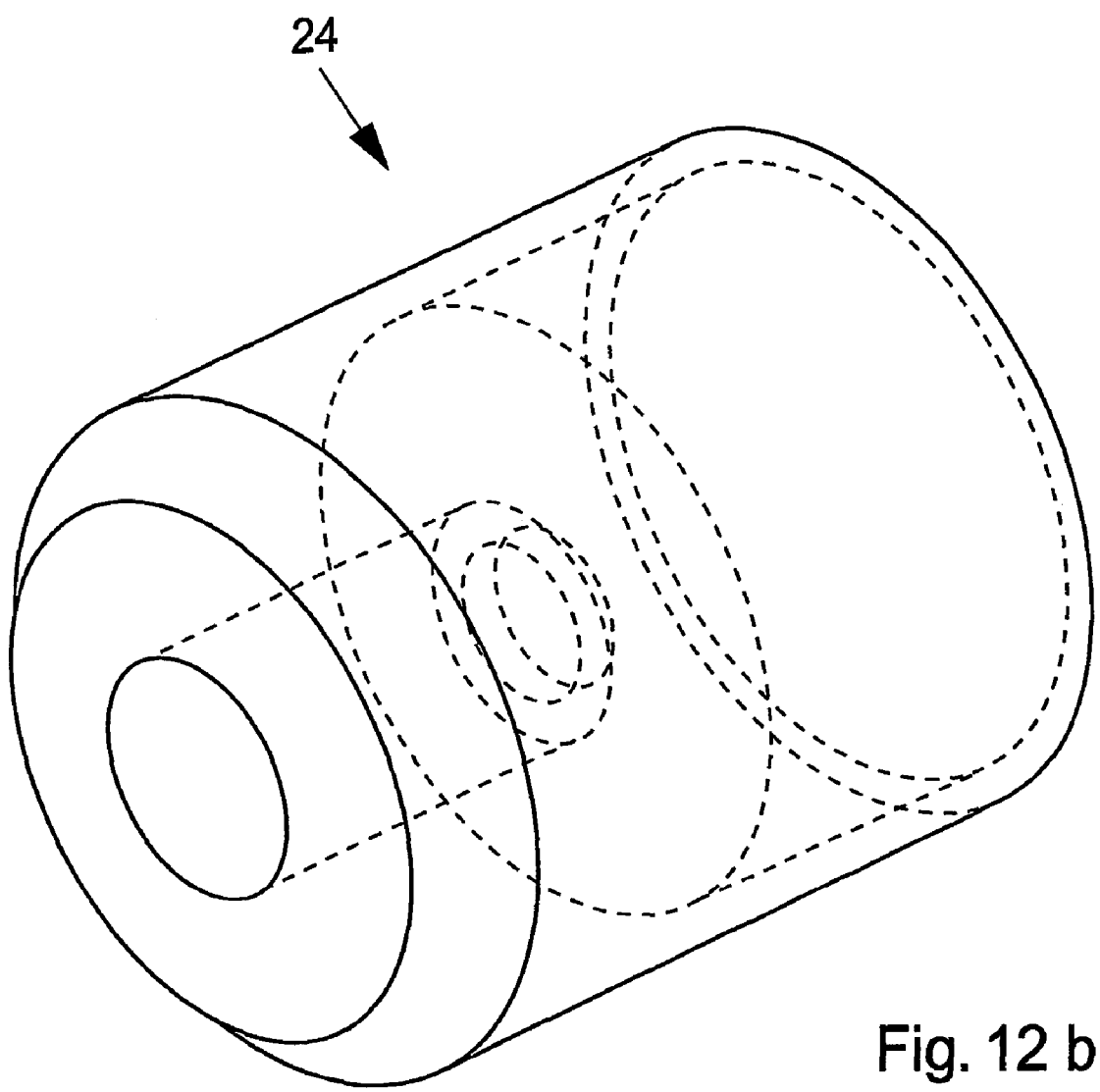
Figure 13:
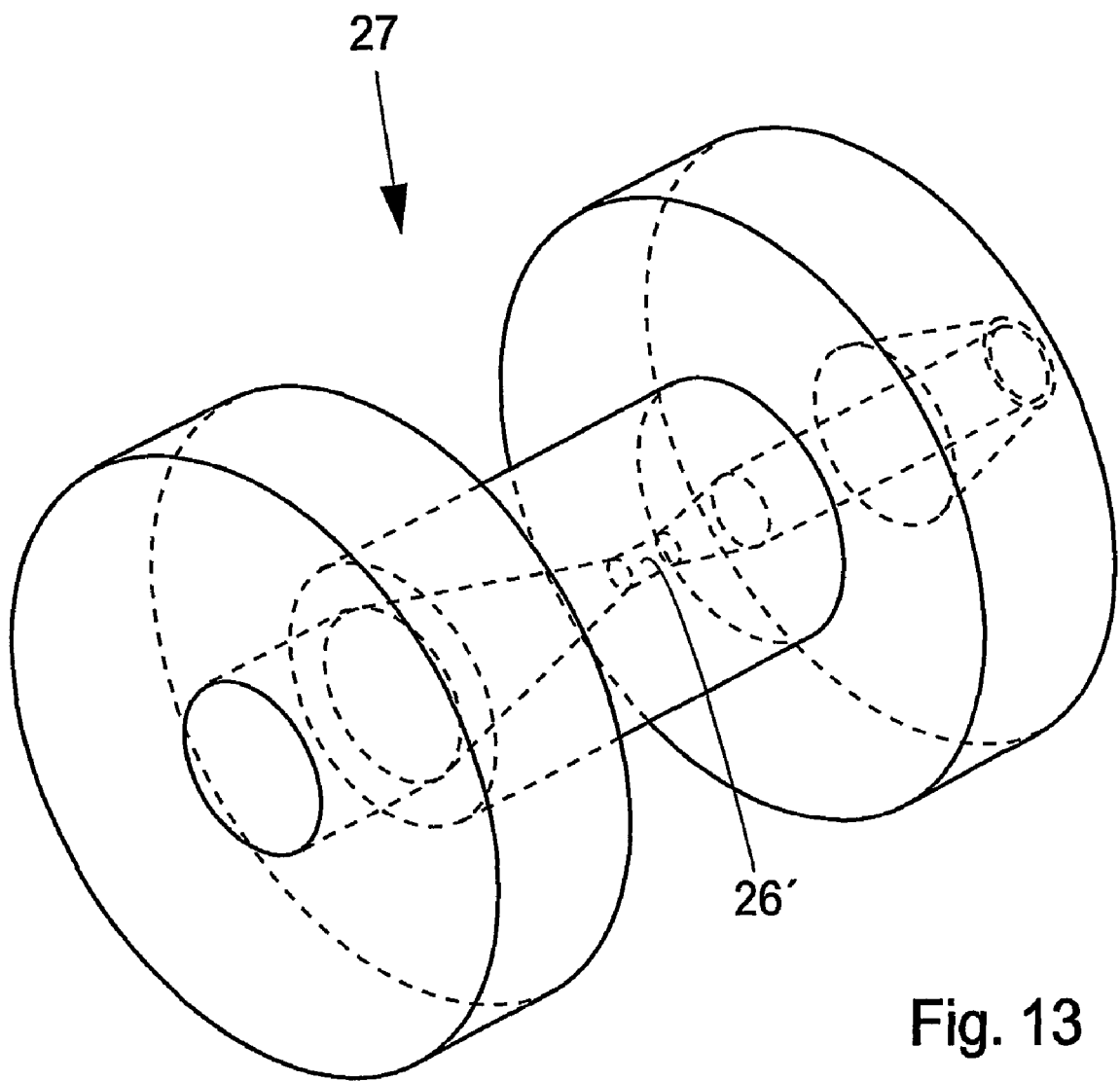

An embodiment of a specimen terminal 22' shown in FIG. 8*a*,8*b* and in FIG. 10 lacks the previously mentioned septum. The specimen terminal 22', which for example can be made of Dacron, is coupled to the guiding device by means of a coupling mechanism 23,24. The coupling mechanism 23,24 comprises a first part 23 (shown in FIG. 12*a*) mounted to the specimen terminal 22' and a second part 24 (shown in FIG. 12*b*) mounted to the first part and to the exterior tube 20 of the guiding device. The coupling mechanism of this embodiment further comprises a valve 27, which is shown in detail in FIG. 13. The valve 27 comprises an internally arranged contraction 26', which preferably is realised as a septum, that the specimen collector has to penetrate in order to engage with the catheter (not shown in FIG. 8*a*,8*b*) in the living test object. In one embodiment this coupling mechanism comprises a swivel and in another embodiment the coupling mechanism is attached to a swivel for movability of the test object.

In FIG. 8*a*,8*b* and in FIG. 11*a*,11*b* there is shown an embodiment of an inlet 60 for compressed air and its main part 61, through which compressed air can be pumped in between the inner tube of the specimen collector 10 and the outer tube 20 of the guiding device 20. Thereby the specimen collector can be pneumatically driven in a selectable direction in the outer tube 20. Shown is also a connector 62 for connecting the outer tubing 20 of the guiding device to the main part 61 of the air inlet 60. As previously explained the compressed air operates against the gaskets or flanges 12 and 23 and possibly the not shown gaskets or flanges 12' and 23', which preferably are annular gaskets in the shape of O-rings.

Disposable Articles

Some of the components, for example the inner tubing or lead of the specimen collector 10 and the outer tubing 20*a*,20*b*,20*c* of the guiding device, are conveniently realised as disposable articles made in suitable materials as mentioned above.

Figure 14:
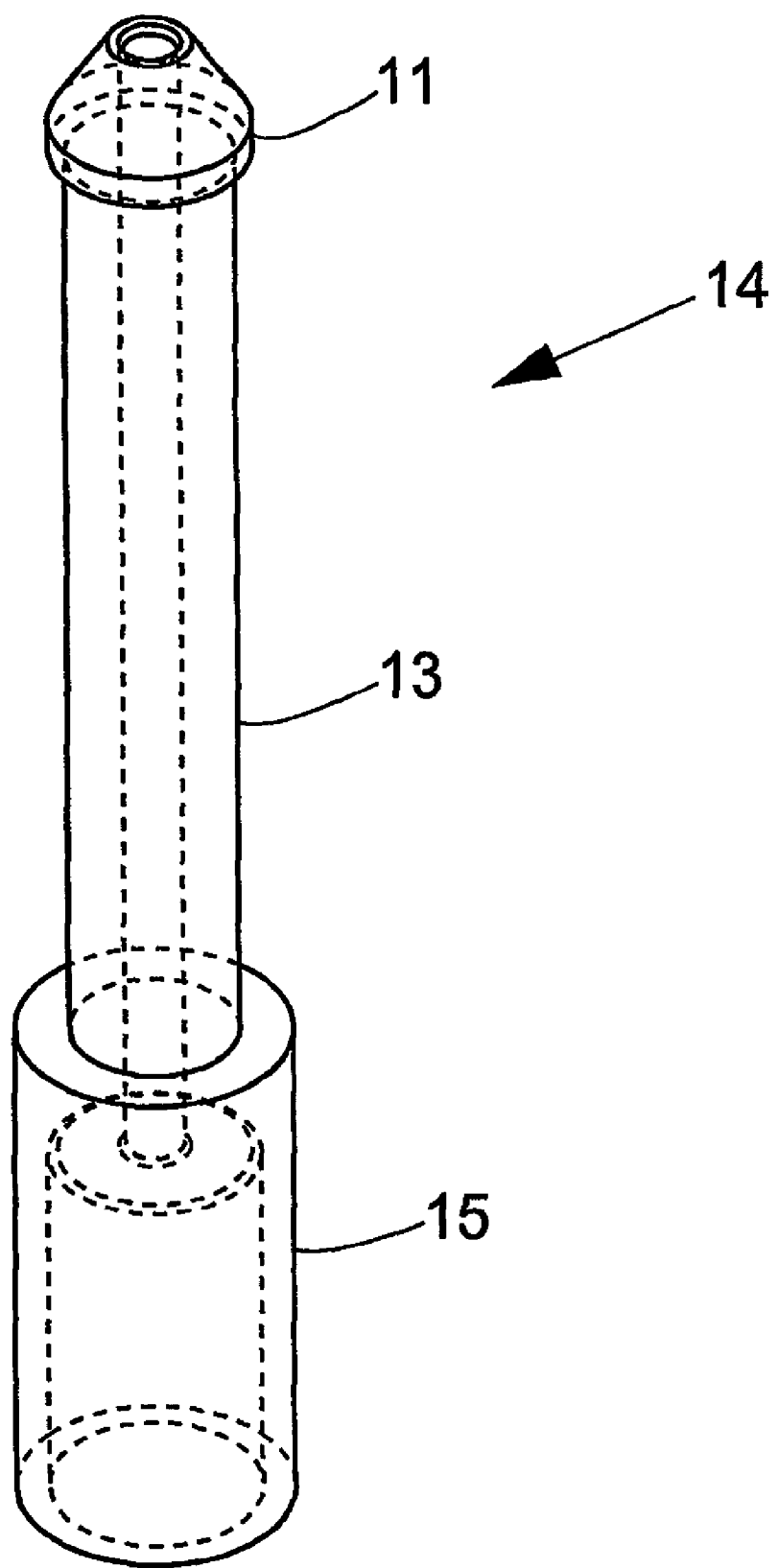

FIG. 14 shows a specimen collector head 14 devised to be mounted at the distal end of a specimen collector in the shape of an inner tubing or a lead having a lumen. The collector head 14 has a specimen storage part 13, a distal widening part 11 having a rounded, tapering or narrowing shape for penetrating a contraction or a septum and a connector 15 for connecting to an inner tubing. The specimen storage part 13 of the specimen collector head is preferably provided with a lumen that has a volume substantially equal to or larger than the wanted sample volume. This specimen storage lumen is further communicatively couplable to the lumen of an inner tube or lead of specimen collector such that the specimen can be sucked into and maintained in said storage part The shown embodiment is realised as an integrated article made in one piece and is advantageously realised as a disposable article in a material having a low or non-adhesive, low or non-reactive and low or non-contaminating characteristics. With this embodiment it is possible to make the inner tubing or lead of the specimen collector that never comes into a direct contact with the specimens in some material having less strict requirements on the adhesive characteristics. In one embodiment the specimen collector head 14 is mounted to the inner tubing close to the gasket 12.

Figure 15:
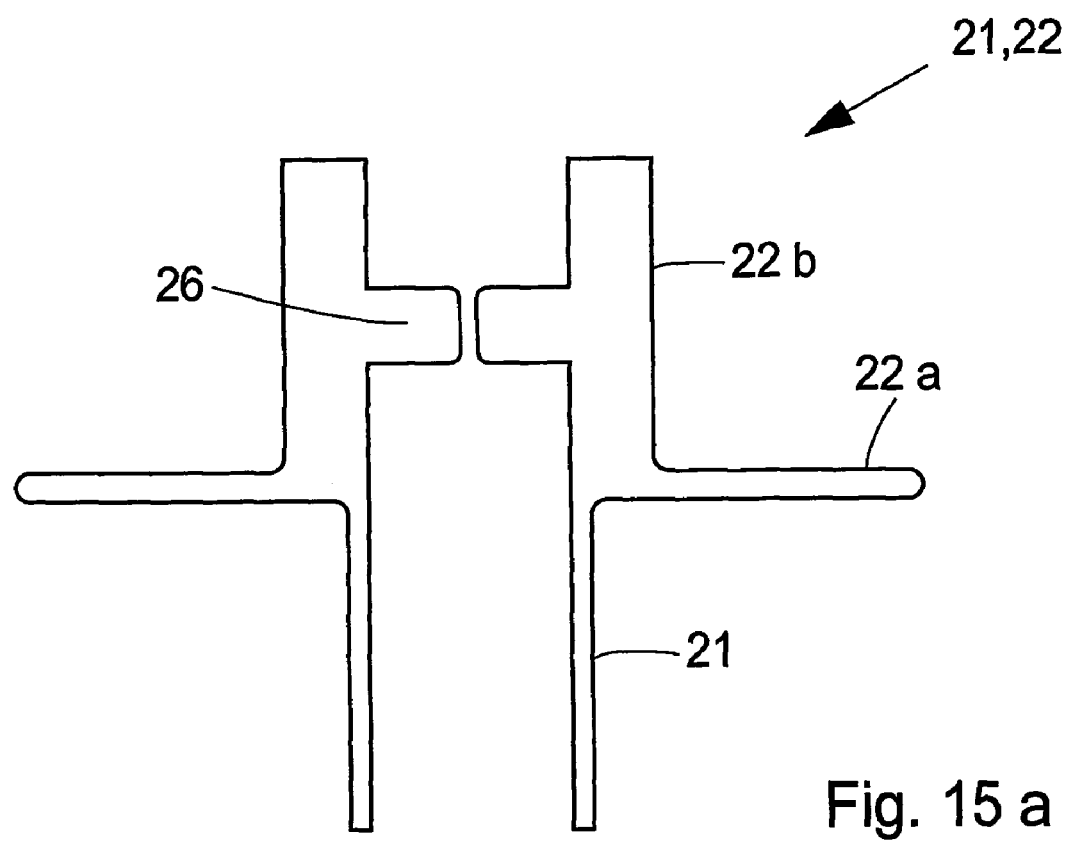
FIG. 15a-15b show schematically embodiments of disposal articles in accordance with the invention.
Figure 15:
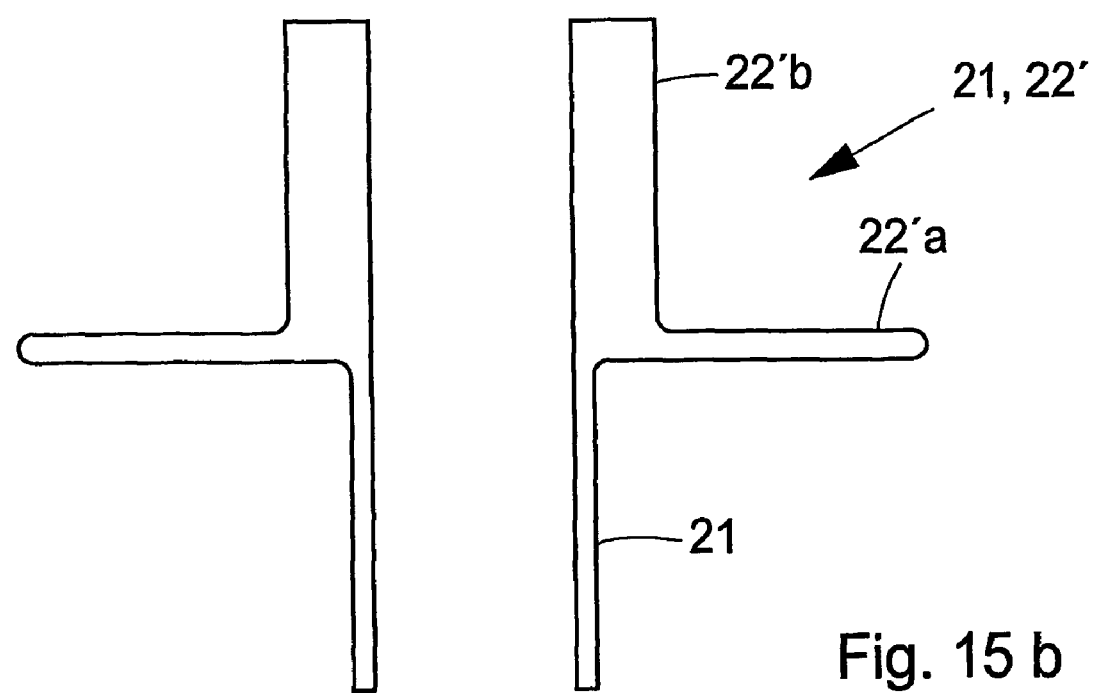

FIG. 15*a* and FIG. 15*b* shows in sectional view embodiments of specimen terminals that are suitable to realise as disposable articles. These embodiments are provided with a connector 22*b*,22'*b* in the shape of a collar for mating with an outer tubing of a guiding device. The connector 22*b*,22'*b* is integrated in one piece with a catheter 21 and a protective flange 22*a*,22'*a*. The variety shown in FIG. 15*a* is provided with contraction 26, whereas the variety in FIG. 15*b* is intended to be used in conjunction with another component having a corresponding contraction or valve functionality.

Other Implementations

The present invention has been described by means of exemplifying embodiments and it should be understood that the invention can be realised in other ways within the scope of the claims.

For example, the outer tubing of the guiding device 20 can comprise a plurality of branches and the guiding path switch can correspondingly be devised to switch between the paths of these branches. Thereby a single automatic specimen taking apparatus can simultaneously operate on a plurality of test objects.

In another example, the specimen collector can be guided by a guiding device, for example in the shape of a wire attached to a static or a living test object. In this case, the specimen collector can be guided to the test object via e.g. loops arranged on the wire and through which the specimen collector is lead. The inventive system can further be realised by means of a tubing having a first channel for a wire attached to the test object and a second channel for the specimen collector.

The invention claimed is:

1. A method for automatic taking of a specimen from a test object, comprising the steps of:
    moving a specimen collector, by means of a guiding device, to a specimen terminal attached to the test object;
    extracting a fluid specimen from the test object to the specimen collector;
    moving The specimen collector, by means of the guiding device, to an output position;
    outputting the specimen from the specimen collector, wherein the guiding device mechanically guides the specimen collector between the specimen terminal and said output position;
    moving the specimen collector by way of a first branch of the guiding device to and from the specimen terminal;
    moving the specimen collector by way of a second branch of the guiding device to and from the specimen container, wherein the specimen collector is moved from the first branch to the second branch via a guiding path switch, wherein the specimen collector comprises an inner tubing that extends inside an outer tubing comprised in the guiding device, the outer tubing having a first end arranged at said specimen terminal and a second end arranged at said specimen collector, wherein the specimen collector is displaced through a first tubing branch of the outer tubing to and from the specimen terminal and through a second tubing branch to and from the specimen container;

moving the inner tubing to a position in a first part of the outer tubing proximal said guiding path switch;

actuating the guiding path switch to join the guiding path of said first tubing part with a selectable guiding path of said first tubing branch or second tubing branch; and moving the inner tubing via said guiding path switch into a selected first or second tubing branch.

2. A system for automatic taking of specimen from a test object, comprising:

an elongate specimen collector having at its distal end a cavity configured to store a liquid specimen from said test object;

a guiding device configured in such a way that said specimen collector can be moved along a selectable first or second guiding path;

a specimen terminal that is attachable to the test object, the specimen terminal being configured to be coupled to a vessel of said test object and to a first guiding path of said guiding device;

wherein the specimen collector comprises a first, interior tubing positioned axially movable in a second, exterior tubing comprised in said guiding device; wherein said exterior tubing has a first orifice at one end coupled to the specimen terminal and a second orifice at another end configured for outputting a content of the specimen collector;

wherein said guiding device comprises a first tubing portion connected at one end to the guiding path switch, a first tubing branch portion and a second tubing branch portion each at one end, respectively, being connected to said guiding path switch; and said first tubing portion is selectively connectable to said first or second tubing branch portion by means of said guiding branch switch.

3. The system as recited in claim 2, wherein said second guiding path is configured to be coupled to a specimen container.

4. The system as recited in claim 2, wherein the guiding device comprises a guiding path switch configured to lead the specimen collector to a first path branch connected to the specimen terminal or to a second path branch for outputting a content of the specimen collector.

5. The system as recited in claim 2, further comprising a pumping device configured to actuate an extraction of a fluid specimen from the test object to the specimen collector and to actuate an output of a fluid specimen from said specimen collector.

6. The system as recited in claim 2, wherein the exterior tubing comprises a perforation configured for insuction of a separation medium, and positioned proximate the connection between the exterior tubing and the specimen terminal.

7. The system as recited in claim 2, further comprising a specimen collector head piece having an elongate shape comprising a lumen for storing a specimen and a connector for connecting to the lumen of a specimen collector tubing or lead.

8. The system as recited in claim 7, further comprising a widening part at one end of the head piece having a generally round geometrical shape, the diameter of which increases from the distal end to a predetermined maximum diameter.

9. The system as recited in claim 2, wherein the specimen terminal has a fluid lumen, a connector for connecting the lumen to a tubing and means for attaching the terminal to a test object.

10. The system as recited in claim 9, the specimen terminal further comprising a flange extending in a substantially radial direction in relation to said lumen of the terminal and being configured to even out a pressure over a surface of the test object when attached to said object.

11. The system as recited in claim 9, the specimen terminal further being devised to be coupled to or comprising a catheter such that a lumen of said catheter coincides with a lumen of said terminal.

12. The system as recited in claim 9, the specimen terminal further being devised to be coupled to or comprising a capillary tube such that a lumen of said capillary tube coincides with a lumen of said terminal.

13. The system as recited in claim 9, the specimen terminal further comprising a contraction.

14. The system as recited in claim 13, wherein the contraction is realised as a septum.

15. The system as recited in claim 13, further comprising a valve element being provided with said contraction.

16. A computer program product stored on a tangible storage medium for use in a data processing system controlling automatic taking of a specimen from a test object by means of a specimen collector guided by a guiding device and displaced by means of a driving mechanism, said test object being coupled at a specimen terminal to the guiding device and said specimen collector having a lumen, the computer program product comprising program code portions configured to direct the data processing system to:

actuate the guiding device and the driving mechanism to move the specimen collector to the specimen terminal;

actuate the extraction of a specimen from the test object into the lumen of said specimen collector by means of a pumping device;

actuate the guiding device and the driving mechanism to move the specimen collector to a selected position;

actuate the output of the specimen from the specimen collector by means of said pumping device, wherein the guiding device mechanically guides the specimen collector between the specimen terminal and said output position;

actuate the movement of the specimen collector by way of a first branch of the guiding device to and from the specimen terminal;

actuate the movement of the specimen collector by way of a second branch of the guiding device to and from the specimen container, wherein the specimen collector is moved from the first branch to the second branch via a guiding path switch, wherein the specimen collector comprises an inner tubing that extends inside an outer tubing comprised in the guiding device, the outer tubing having a first end arranged at said specimen terminal and a second end arranged at said specimen collector, wherein the specimen collector is displaced through a first tubing branch of the outer tubing to and from the specimen terminal and through a second tubing branch to and from the specimen container;

actuate the movement of the inner tubing to a position in a first part of the outer tubing proximal said guiding path switch;

actuate the guiding path switch to join the guiding path of said first tubing part with a selectable guiding path of said first tubing branch or second tubing branch; and to actuate the movement of the inner tubing via said guiding path switch into a selected first or second tubing branch.

17. The computer program product as recited in claim 16, further comprising program code portions configured to direct a data processing system of a specimen taking system.

* * * * *